(12) United States Patent
Kaku et al.

(10) Patent No.: US 12,213,788 B2
(45) Date of Patent: Feb. 4, 2025

(54) SEAT SYSTEM AND PROGRAM

(71) Applicant: TS TECH CO., LTD., Asaka (JP)

(72) Inventors: Hiroyuki Kaku, Tochigi (JP); Takako Miyoshi, Tochigi (JP); Ryosuke Sato, Tochigi (JP); Yoshikazu Ito, Tochigi (JP); Satoshi Suzuki, Tochigi (JP); Munetaka Kowa, Tochigi (JP)

(73) Assignee: TS TECH CO., LTD., Saitama (JP)

( * ) Notice: Subject to any disclaimer, the term of this patent is extended or adjusted under 35 U.S.C. 154(b) by 732 days.

(21) Appl. No.: 17/430,825

(22) PCT Filed: Jan. 14, 2020

(86) PCT No.: PCT/JP2020/000793
§ 371 (c)(1),
(2) Date: Aug. 13, 2021

(87) PCT Pub. No.: WO2020/166248
PCT Pub. Date: Aug. 20, 2020

(65) Prior Publication Data
US 2022/0047197 A1 Feb. 17, 2022

(30) Foreign Application Priority Data

Feb. 14, 2019 (JP) .................................. 2019-024084
Feb. 14, 2019 (JP) .................................. 2019-024093

(51) Int. Cl.
*A61B 5/18* (2006.01)
*A61B 5/00* (2006.01)
*A61B 5/11* (2006.01)

(52) U.S. Cl.
CPC .............. *A61B 5/18* (2013.01); *A61B 5/1116* (2013.01); *A61B 5/6887* (2013.01); *A61B 5/74* (2013.01); *A61B 2562/0247* (2013.01)

(58) Field of Classification Search
CPC ....... A61B 5/1036; A61B 5/116; A61B 5/162; A61B 5/18; A61B 5/6887; A61B 5/6891;
(Continued)

(56) References Cited

U.S. PATENT DOCUMENTS 9,795,322 B1 * 10/2017 Karunaratne ........ A61B 5/6891
10,272,282 B2    4/2019 Harlow
(Continued)

FOREIGN PATENT DOCUMENTS

CN          107077603 A      8/2017
JP          2001340163 A    12/2001
(Continued)

OTHER PUBLICATIONS

Office Action issued for corresponding Chinese Patent Application No. 202080014642.0, issued Jan. 19, 2024, 18 pages, English translation provided.
(Continued)

*Primary Examiner* — Eric F Winakur
*Assistant Examiner* — Abel Seifu Abegaz
(74) *Attorney, Agent, or Firm* — HSML P.C.

(57) ABSTRACT

Provided are a seat system and a computer program product by which an occupant seated on a seat can grasp his/her own reflexes or the like. The seat system includes a seat which includes a seat body, and a sensor configured to acquire information for use in detecting motion of an occupant seated on the seat body, and a terminal configured to acquire the information from the sensor. The terminal outputs an instruction to prompt the occupant to make a predetermined motion, makes a determination based on the information acquired from the sensor as to whether or not the occupant has made the predetermined motion, and notifies the occupant of a response time elapsed between outputting the
(Continued)

instruction and making the predetermined motion, and/or a performance level evaluated based on the response time.

10 Claims, 16 Drawing Sheets

(58) Field of Classification Search
CPC .. A61B 5/6893; A61B 5/74; A61B 2562/0247
See application file for complete search history.

(56) References Cited

U.S. PATENT DOCUMENTS

| | | | |
|---|---|---|---|
| 10,540,017 | B2 | 1/2020 | Goto et al. |
| 2015/0261309 | A1 | 9/2015 | Goto et al. |
| 2016/0354027 | A1* | 12/2016 | Benson ................. A61B 5/7282 |
| 2017/0251979 | A1 | 9/2017 | Franz et al. |
| 2017/0367655 | A1* | 12/2017 | Sugiyama ............... A61B 5/113 |
| 2018/0078812 | A1 | 3/2018 | Harlow |
| 2019/0209886 | A1 | 7/2019 | Harlow |
| 2019/0343428 | A1* | 11/2019 | De Vries .............. A61B 5/6891 |

FOREIGN PATENT DOCUMENTS

| | | |
|---|---|---|
| JP | 2003038443 | 2/2003 |
| JP | 2004181179 A | 7/2004 |
| JP | 2006149911 | 6/2006 |
| JP | 2006325755 A | 12/2006 |
| JP | 2015176367 | 10/2015 |
| JP | 2017065504 | 4/2017 |
| JP | 2017176302 | 10/2017 |
| JP | 2018166935 | 11/2018 |
| KR | 20160094060 A | 8/2016 |
| WO | 2009069756 | 6/2009 |

OTHER PUBLICATIONS

International Search Report and Written Opinion issued for International Patent Application No. PCT/JP2020/000793, Date of mailing: Mar. 31, 2020, 22 pages including English translation.

Notification of Reason(s) for Refusal issued for Japanese Patent Application No. 2019-024084, Dispatch Date: Jan. 31, 2023, 9 pages including English translation.

Notification of Reason(s) for Refusal issued for Japanese Patent Application No. 2019-024093, Dispatch Date: Feb. 21, 2023, 9 pages including English translation.

Second Office Action issued for Chinese Patent Application No. 202080014642.0, dated Jun. 7, 2024, 45 pages including English machine translation.

Notice of Reasons for Refusal issued for Japanese Patent Application No. 2024-011507, Dispatch date: Nov. 26, 2024, 6 pages including English machine translation.

* cited by examiner

FIG.4
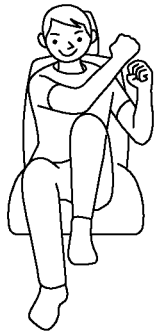

FIG.8
(a) BOTH-KNEE LIFT
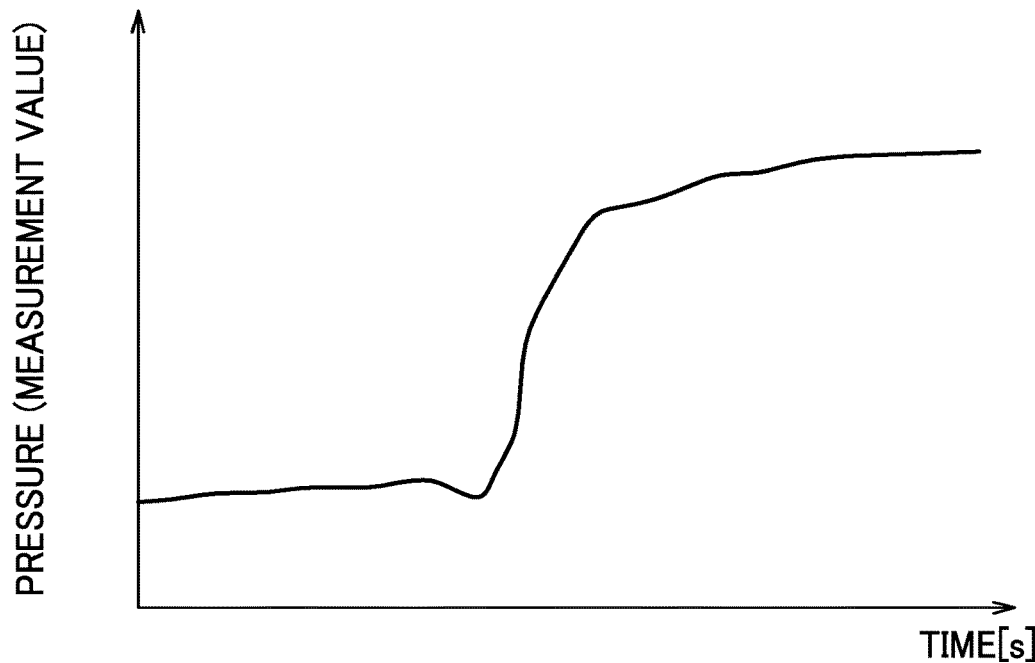
(b) BOTH-KNEE LIFT
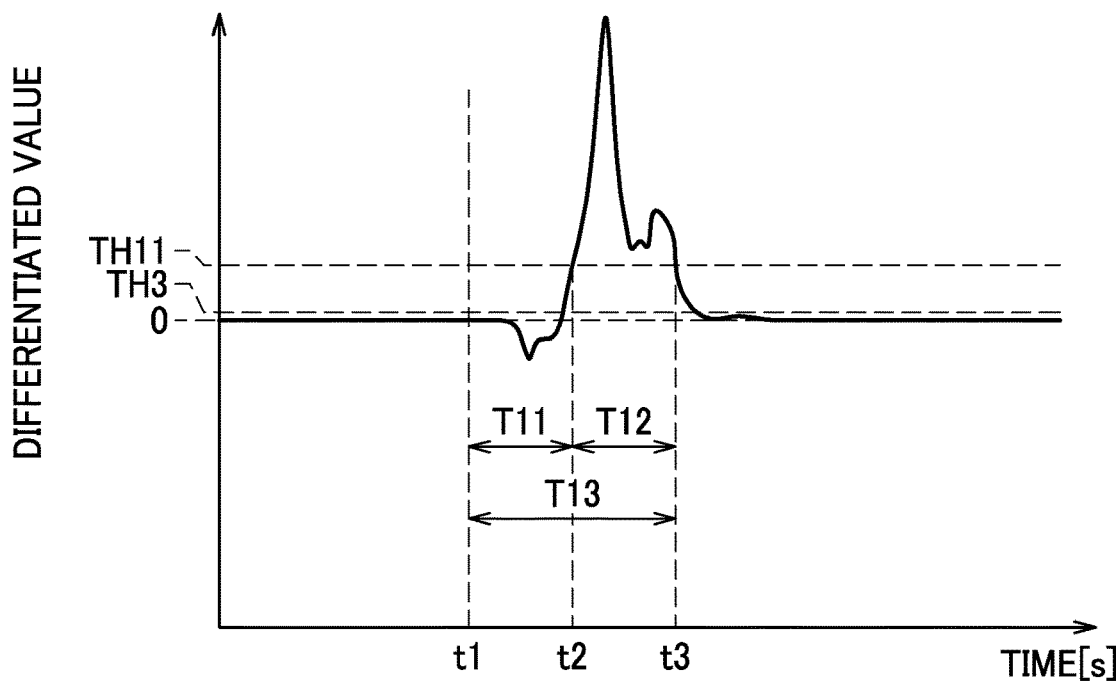

FIG.9
(a) LEFT-KNEE LIFT
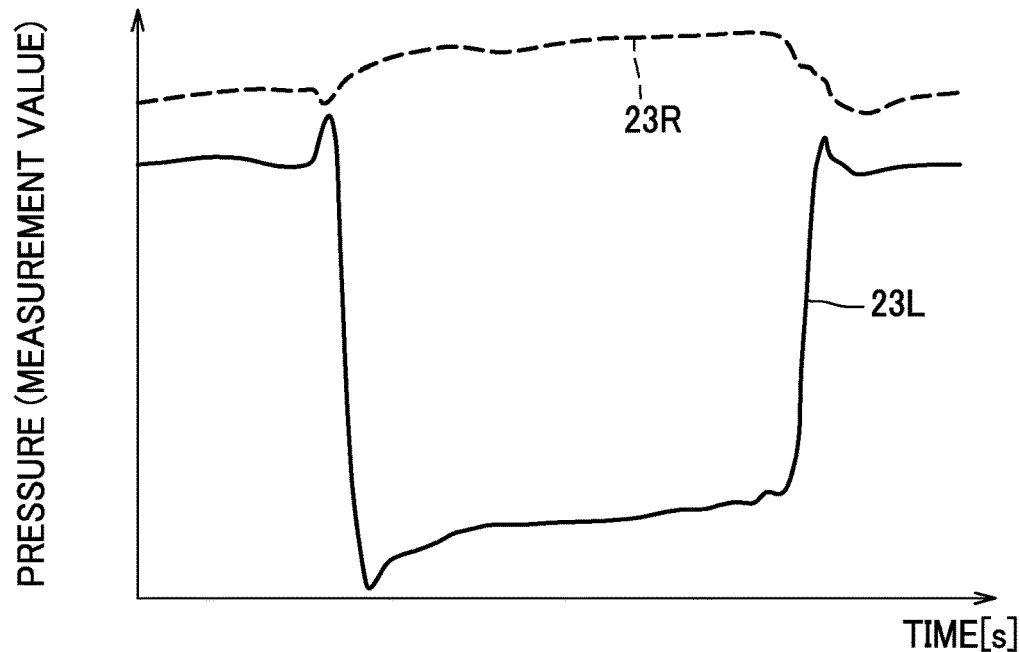
(b) LEFT-KNEE LIFT
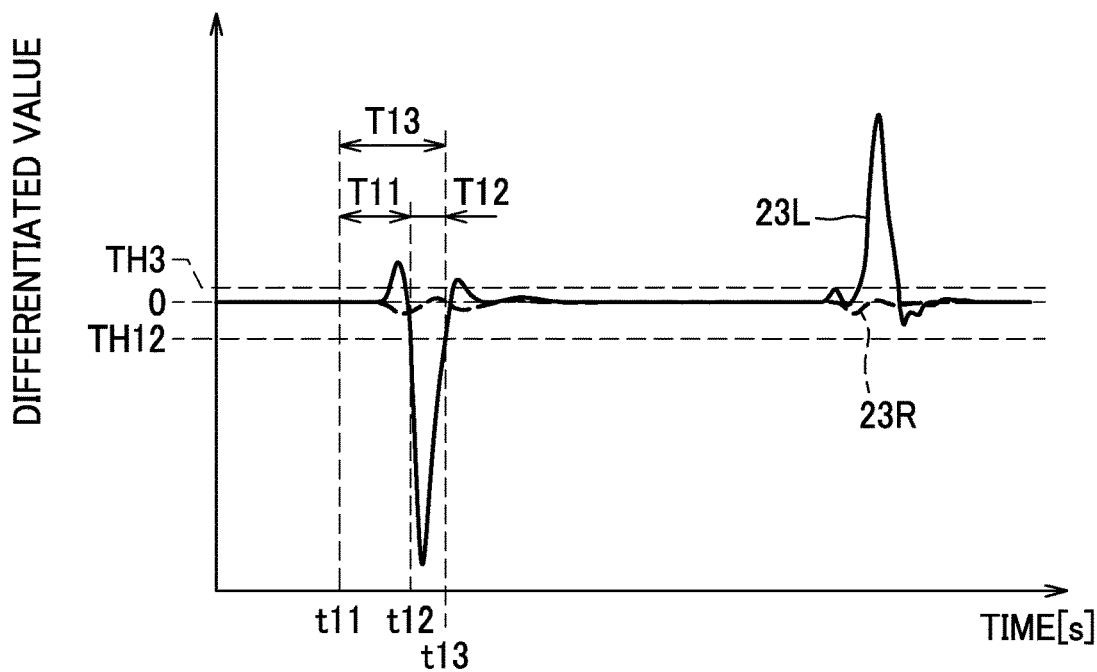

FIG.10
(a) RIGHT-KNEE LIFT
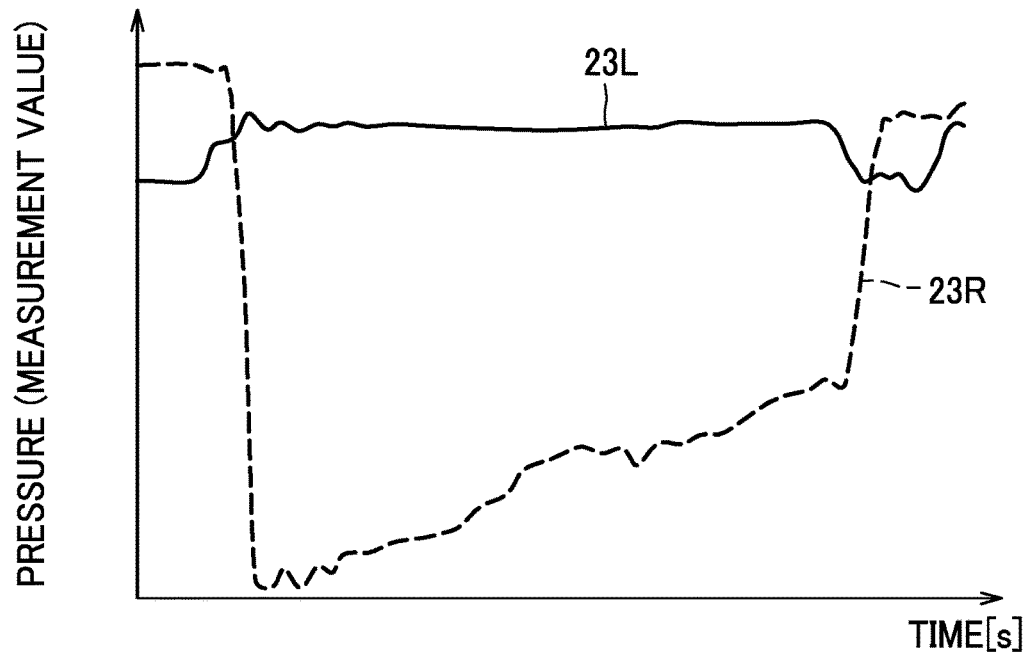
(b) RIGHT-KNEE LIFT
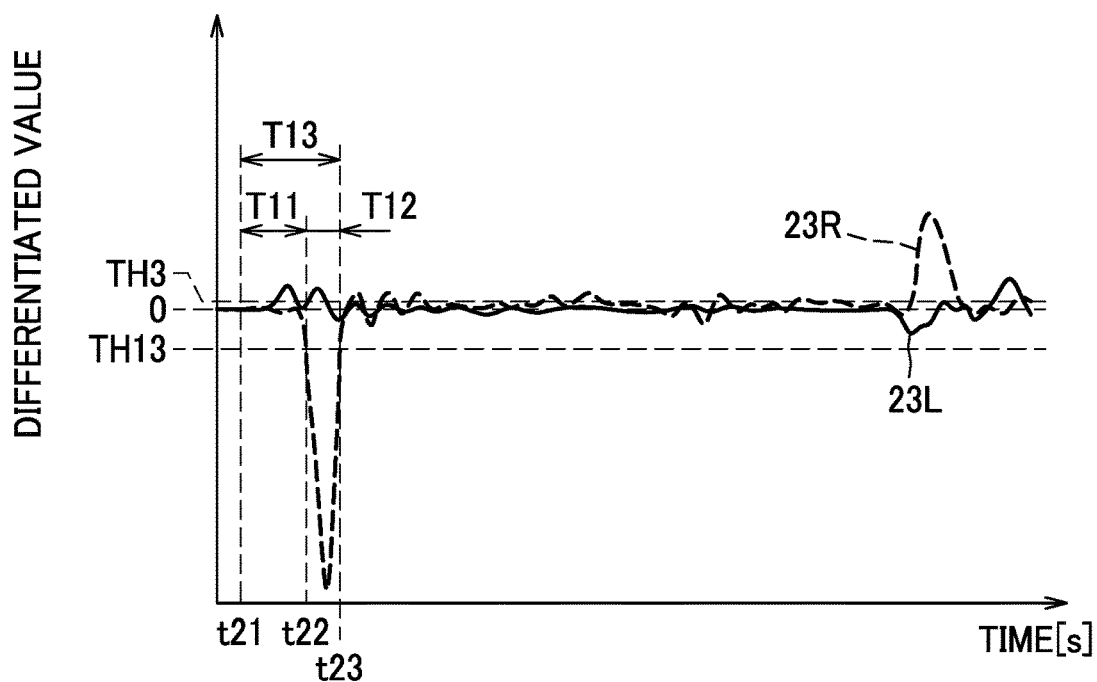

FIG.11

| | LIFT UP LEFT KNEE | LIFT UP BOTH KNEES | LIFT UP RIGHT KNEE | AVERAGE |
|---|---|---|---|---|
| | BEST TIME [s] | BEST TIME [s] | BEST TIME [s] | |
| REACTION TIME [s] | 0.4 | 0.7 | 1.1 | 0.7 |
| MOTION TIME [s] | 0.4 | 0.7 | 1.1 | 0.7 |
| MOTION COMPLETION TIME [s] | 0.8 | 1.4 | 2.2 | 1.4 |
| PERFORMANCE LEVEL | Excellent | Good | Bad | Good |

SEAT SYSTEM AND PROGRAM

TECHNICAL FIELD

This disclosure relates to a seat system including a seat with a sensor, and a program for causing a terminal to operate based on information acquired from the seat with the sensor.

BACKGROUND ART

A car seat with a plurality of pressure sensors located on the seat to detect a seated occupant's posture is hitherto known in the art (see JP 2017-65504 A).

SUMMARY OF INVENTION

Although the car seat of JP 2017-65504 A merely evaluates the seating posture of a driver, information acquired from the sensor provided in the seat could possibly be utilized more effectively.

From this point of view, this paper for detailed description proposes, for the purpose of creating a new value of a seat, a seat system and a program by which an occupant seated on the seat can grasp his/her own reflexes (response speed).

On the other hand, training equipment including a sensor, for use in rehabilitation, resistance (muscular) exercise training, or the like is hitherto known in the art. For example, JP 2018-166935 A discloses equipment for controlling a resistance in accordance with the physical state of a user. This training equipment is provided with a plurality of electrodes attached to the body of a user for measurement, so that the resistance is adjusted in accordance with a waveform pattern of the cardiogram acquired therefrom.

However, this training equipment requires attachment of sensors to the body of a user for detecting the physical state of the user, which would make a user unable to take exercise in a relaxed state, uncomfortable about sanitary conditions, or otherwise feel uneasy.

It would be desirable that biological parameters of a user be acquired and utilized without attachment of a sensor to his/her body during use.

In one aspect, a seat system including a seat and a terminal is disclosed. The seat includes a seat body and a sensor. The sensor is provided at the seat body, and configured to acquire information for use in detecting motion of an occupant seated on the seat body. The terminal is configured to acquire the information from the sensor.

The terminal is configured to output an instruction to prompt the occupant to make a predetermined motion, make a determination based on the information acquired from the sensor as to whether or not the occupant has made the predetermined motion, and notify the occupant of a response time elapsed between outputting the instruction and making the predetermined motion and/or a performance level evaluated based on the response time.

In another aspect, a program to be executed on a terminal capable of acquiring information from a sensor provided at a seat body is disclosed. Herein, the program refers to a set of instruction modules that are stored in a computer-readable storage medium accessible by the terminal as a computer having a processor, and thus can be loaded and executed by the terminal (i.e., processor). The program causes the terminal to execute an instruction step of outputting an instruction to prompt an occupant seated on the seat body to make a predetermined motion, an acquisition step of acquiring the information from the sensor, a determination step of making a determination based on the information acquired from the sensor as to whether or not the occupant has made the predetermined motion, and a notification step of notifying the occupant of a response time elapsed between outputting the instruction and making the predetermined motion and/or a performance level evaluated based on the response time. The program is stored on a computer-readable storage medium and provided for use.

With the seat system or program as described above, when an occupant seated on the seat has made a predetermined motion in accordance with an instruction from the terminal, the terminal notifies the occupant of the response time elapsed between outputting the instruction and making the predetermined motion, and/or other information. Accordingly, the occupant seated on the seat can grasp his/her own reflexes.

The aforementioned response time may include at least one of a reaction time elapsed between outputting the instruction and starting the predetermined motion, and a motion completion time elapsed between outputting the instruction and completion of the predetermined motion.

With this configuration, as the response time includes at least one of the reaction time and the motion completion time, the occupant's reflexes can be adequately quantified.

The terminal may be configured to determine the performance level by comparison made between the response time as computed and a reference response time as stored.

With this configuration, the occupant can be notified of the performance level evaluated based on the reference response time, and thus can grasp the level of his/her reflexes or ability to react quickly.

The sensor may include a pressure sensor, and the terminal may be configured to make the determination, based on a change in pressure acquired from the pressure sensor, as to whether or not the occupant has made the predetermined motion.

With this configuration, by making use of the pressure value acquired from the pressure sensor, the occupant's motion can be determined adequately.

The terminal may be configured to compute a differentiated value of a signal acquired from the sensor, and make a determination that the predetermined motion has been started, on condition that a magnitude of the differentiated value has crossed a first threshold. In other words, the determination step may comprise computing a differentiated value of a signal acquired from the sensor, and making a determination that the predetermined motion has been started, on condition that a magnitude of the differentiated value has crossed a first threshold.

With this configuration, the starting of the predetermined motion can be determined adequately based on the differentiated value; therefore, the reaction time elapsed between outputting the instruction and starting the predetermined motion can be determined precisely as the response time, and evaluated adequately.

The terminal may be configured to make a determination that the predetermined motion has been completed, on condition that the magnitude of the differentiated value has crossed the first threshold and then become smaller than a second threshold not higher than the first threshold. In other words, the determination step may comprise making a determination that the predetermined motion has been completed, on condition that the magnitude of the differentiated value has crossed the first threshold and then become smaller than a second threshold not greater than the first threshold.

With this configuration, the completion of the predetermined motion can be determined adequately based on the differentiated value; therefore, the motion completion time elapsed between outputting the instruction and completion of the predetermined motion can be determined precisely as the response time, and evaluated adequately.

The terminal may be configured to output the instruction on condition that a magnitude of a differentiated value of a signal acquired from the sensor has become smaller than a third threshold. In other words, the instruction step may comprise outputting the instruction on condition that a magnitude of a differentiated value of a signal acquired from the sensor has become smaller than a third threshold.

With this configuration, an instruction to prompt the occupant to make the predetermined motion can be outputted when the occupant stays almost still; therefore the reflexes can be determined precisely.

The terminal may be configured to output the instruction as chosen randomly from among a plurality of instructions. In other words, the instruction step may comprise outputting the instruction as chosen randomly from among a plurality of instructions.

With this configuration, the occupant can be instructed to make different motions; therefore, the occupant can be notified of his/her reflexes for the respective motions.

The terminal may be configured to execute a plurality of rounds of a process comprising outputting the instruction and computing the response time, to notify the occupant of an average of response times acquired in the plurality of rounds, and/or a performance level evaluated based on the average of the response times.

With this configuration, the occupant can be notified of the average of response times or the like resulting from a plurality of rounds of the process of outputting the instruction and computing the response time; therefore, the occupant can know the average of his/her reflexes.

Further, a server capable of communication with the terminal may be provided, and the terminal may be configured to keep recorded therein an attribute of the occupant, and to transmit the response time as computed and the attribute of the occupant, to the server, and the server may be configured to accumulate the attribute and the response time for the occupant.

With this configuration, in which the attribute and the response time for the occupant are accumulated, the response time for the occupant can be compared, for example, with the response times for others having the same attributes as the attribute of the occupant.

In still another aspect, a training seat is disclosed. The training seat comprises a seat body, a sensor, an exercise device for a user to take exercise, and a controller. The sensor is provided at the seat body, and configured to acquire biological information on a user seated on the seat body. The exercise device is provided integrally with or separably outside of the seat body. The controller is connected to the sensor.

The controller is configured to acquire the biological information from the sensor, and notify the user of information related to a state of exercise of the user based on the biological information.

With this configuration, the controller notifies the user of information about the state of exercise based on the biological information acquired from the sensor; therefore, the user who is taking training can know the state of exercise. Since the sensor for acquiring the biological information on the user is provided at the seat body, the user is not required to have the sensor attached to his/her body. Therefore, the user can take training in a relaxed state without concern for the sensor. Thus-obviated necessity of attaching the sensor to the body may ease user's apprehensions about sanitary conditions.

In the training seat as described above, the sensor may comprise a pressure sensor, and the controller may be configured to evaluate a user's posture during exercise by comparing a pressure value with a predetermined criterion.

With this configuration, the user's posture during exercise can be evaluated by comparison with the predetermined criterion and presented for notification. Therefore, the user can try to assume a good posture for training.

To present another aspect of the training seat, a training seat comprising a seat body, a sensor, an exercise device for a user to take exercise, and a controller is disclosed. The sensor is provided at the seat body, and configured to acquire biological information on a user seated on the seat body. The exercise device is provided integrally with or separably outside of the seat body. The controller is connected to the sensor and connected to the exercise device in such a manner as to be capable of controlling a resistance of the exercise device.

The controller may be configured to acquire biological information from the sensor, and control the resistance of the exercise device based on the biological information.

With this configuration, in which the controller controls the resistance of the exercise device based on the biological information acquired from the sensor, the user can take an effective training with a properly-controlled resistance. Since the sensor for acquiring the biological information on the user is provided at the seat body, the user is not required to have the sensor attached to his/her body. Therefore, the user can take training in a relaxed state without concern for the sensor. Thus-obviated necessity of attaching the sensor to the body may ease user's apprehensions about sanitary conditions.

In the training seat as described above, the controller may preferably be configured to reduce the resistance of the exercise device if it is determined, based on the biological information, that exercise stress on the user is greater than a predetermined reference value.

The controller may preferably be configured to increase the resistance of the exercise device if it is determined, based on the biological information, that the exercise stress on the user is smaller than a predetermined reference value.

In the training seat as described above, the biological information may include at least one of pressure, temperature, humidity, pulse, and perspiration from the user, and a heart rate of the user.

BRIEF DESCRIPTION OF DRAWINGS

FIG. 4 is a diagram showing an initial screen for prompting an occupant to assume a reference posture.

FIG. 8 includes (a) a graph showing change of pressure values caused when an occupant makes a both-knee-lift-up motion, and (b) a graph showing differentiated values of the pressure values.

FIG. 9 includes (a) a graph showing change of pressure values caused when an occupant makes a left-knee-lift-up motion, and (b) a graph showing differentiated values of the pressure values.

FIG. 10 includes (a) a graph showing change of pressure values caused when an occupant makes a right-knee-lift-up motion, and (b) a graph showing differentiated values of the pressure values.

FIG. 11 is a diagram showing a screen displaying the results of measurement of the reflexes.

DESCRIPTION OF EMBODIMENTS

Next, a detailed description will be given of a first embodiment with reference made to the drawings where appropriate.

Figure 1:
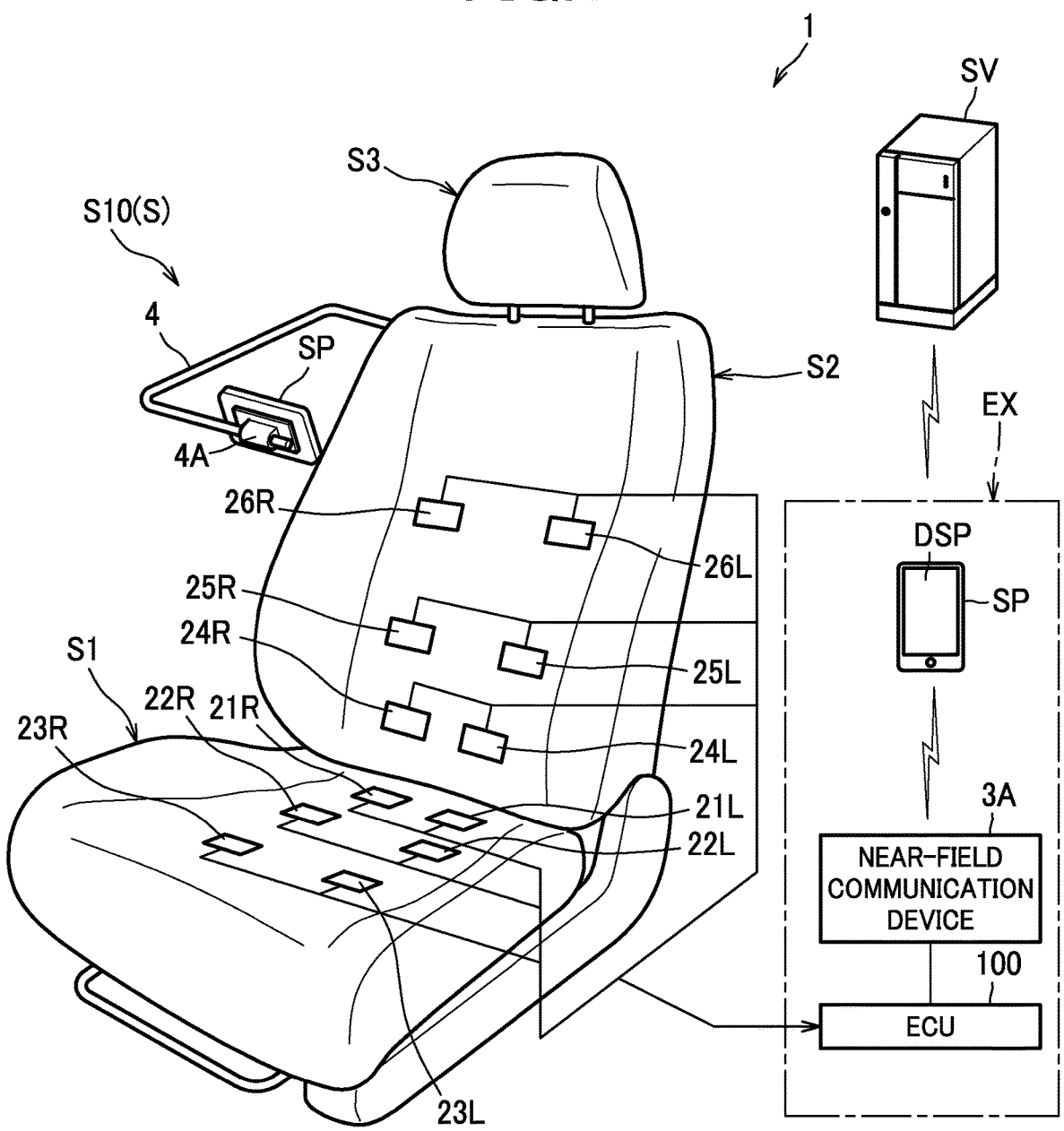
FIG. 1 is a diagram showing a seat system according to a first embodiment.

As shown in FIG. 1, a seat system 1 of the present embodiment includes a seat S, a seat experience device EX, and a server SV.

The seat S includes a seat body S10 and pressure sensors 21 to 26. The seat body S10 is, as an example, a vehicle seat to be installed in a car or other vehicles, and includes a seat bottom S1, a seat back S2, and a headrest S3. The seat bottom S1 and the seat back S2 have outer coverings under which a plurality of pressure sensors 21 to 26 are provided. The pressure sensors 21 to 26 are configured as a sensor to detect motion of an occupant seated on the seat body S10.

The pressure sensors 21 to 26 are so arranged as to be capable of detecting a state of a seat surface facing an occupant seated on the seat body S10, to acquire values of pressure from the occupant seated on the seat body S10. An ECU (electronic control unit) 100 is a device that exercises control over an operation of the seat body S10 (e.g., over a motor for an electrically powered reclining mechanism, or a heater, etc., not illustrated), and is connected to the pressure sensors 21 to 26 and thereby made capable of acquiring measurement values from the pressure sensors 21 to 26.

The respective pressure sensors 21 to 26 are provided in pairs, i.e., each located left and right, symmetric with respect to a laterally central position of the seat S. In the following description and drawings which will be referred to below, pressure sensors 21 to 26 located on the left side may be designated by reference characters with "L" appended thereto, and pressure sensors 21 to 26 located on the right side may be designated by reference characters with "R" appended thereto, so that distinctions are drawn therebetween.

In the seat bottom S1, the pressure sensors 21 to 23 are provided.

The pressure sensors 21 are provided in positions corresponding to the lowermost portions of ischial bones of the occupant. On these positions, the load of the occupant is borne largest.

The pressure sensors 22 are located a little frontward of the pressure sensors 21.

The pressure sensors 21 and the pressure sensors 22 are provided so that each pair of the pressure sensors 21, 22 measures the pressure from the buttocks of the occupant, and only one pair may be provided.

The pressure sensors 23 are located frontward of and distanced far from the pressure sensors 21 and the pressure sensors 22. The pressure sensors 23 are located under the thighs of the occupant, and capable of determining values of pressure from the thighs of the occupant.

In the seat back S2, the pressure sensors 24 to 26 are provided. The pressure sensors 24 are provided in positions corresponding to the back of the lumbar region of the occupant.

The pressure sensors 25 are located in positions a little higher than the positions of the pressure sensors 24.

The pressure sensors 24 and the pressure sensors 25 are provided so that each pair of the pressure sensors 24, 25 measures the pressure from the lumbar region of the occupant, and only one pair may be provided.

The pressure sensors 26 are located above and distanced far from the pressure sensors 24 and the pressure sensors 25. The pressure sensors 26 are located in positions corresponding to the shoulders of the occupant, and capable of determining values of pressure from the shoulders of the occupant.

In the present embodiment, the seat system 1 is configured to provide a game to measure reflexes using the pressure sensors 21 to 26. In the present embodiment, the pressure sensors 21 to 26 are an example of a sensor configured to acquire a measurement value for use in detecting motion of an occupant seated on the seat body S10. The game to measure reflexes is a game in which an occupant seated on the seat body S10 can measure his/her reflexes by imitating poses of an illustrated character or following an instructive message shown on a display DSP of a smartphone SP.

The seat body S10 is provided with a holder 4 for holding a smartphone SP. The holder 4 is formed by bending a wire, with one end fixed to the seat back S2 and other end having a retaining portion 4A for the smartphone SP to be retained thereto. With the smartphone SP being retained to the retaining portion 4A, the occupant can see the display DSP of the smartphone SP without holding the smartphone SP by hand. Accordingly, the occupant can make motions using his/her whole body as instructed in the game to measure reflexes while watching the display DSP.

The seat experience device EX is configured to include the ECU 100 and the smartphone SP as an example of a terminal.

A near-field communication device 3A which enables near-field wireless communication, such as Bluetooth (registered trademark), Wi-Fi (registered trademark), etc. is connected to the ECU 100. The ECU 100 is connected to the pressure sensors 21 to 26.

The ECU 100, the smartphone SP, and the server SV each include a CPU, a ROM, a RAM, a rewritable nonvolatile memory, etc. (not shown), and are configured such that the CPU loads into the RAM and executes programs stored beforehand in a storage medium (ROM, rewritable nonvolatile memory, etc.). The smartphone SP further includes the display DSP. The smartphone SP is configured to operate according to the program, so that the steps for executing the game to measure reflexes are executed by the smartphone SP.

To be more specific, the smartphone SP has a function of acquiring measurement values from the respective pressure sensors 21 to 26 via the near-field communication device 3A and the ECU 100, and executing the game to measure reflexes based on the acquired measurement values. The smartphone SP is configured to be capable of communicating with the server SV via the Internet.

The smartphone SP has a function of outputting an instruction to prompt an occupant to make a predetermined motion during the game to measure reflexes. To be more specific, the smartphone SP is configured to output an instruction as chosen randomly from among a plurality of instructions, as the instruction to prompt an occupant to make a predetermined motion.

Figure 5:
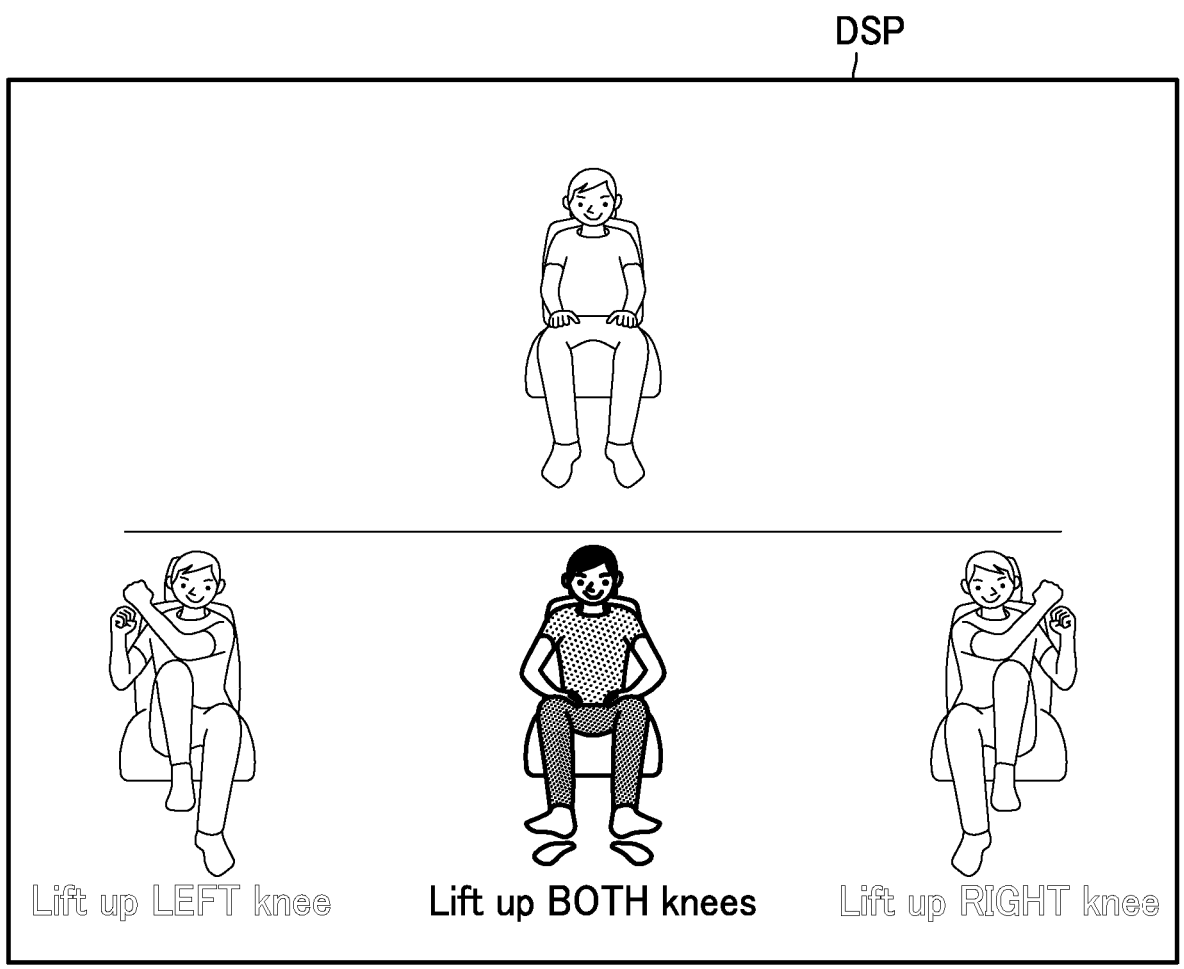
FIG. 5 is a diagram showing a screen for instruction to make a both-knee-lift-up motion.
Figure 6:
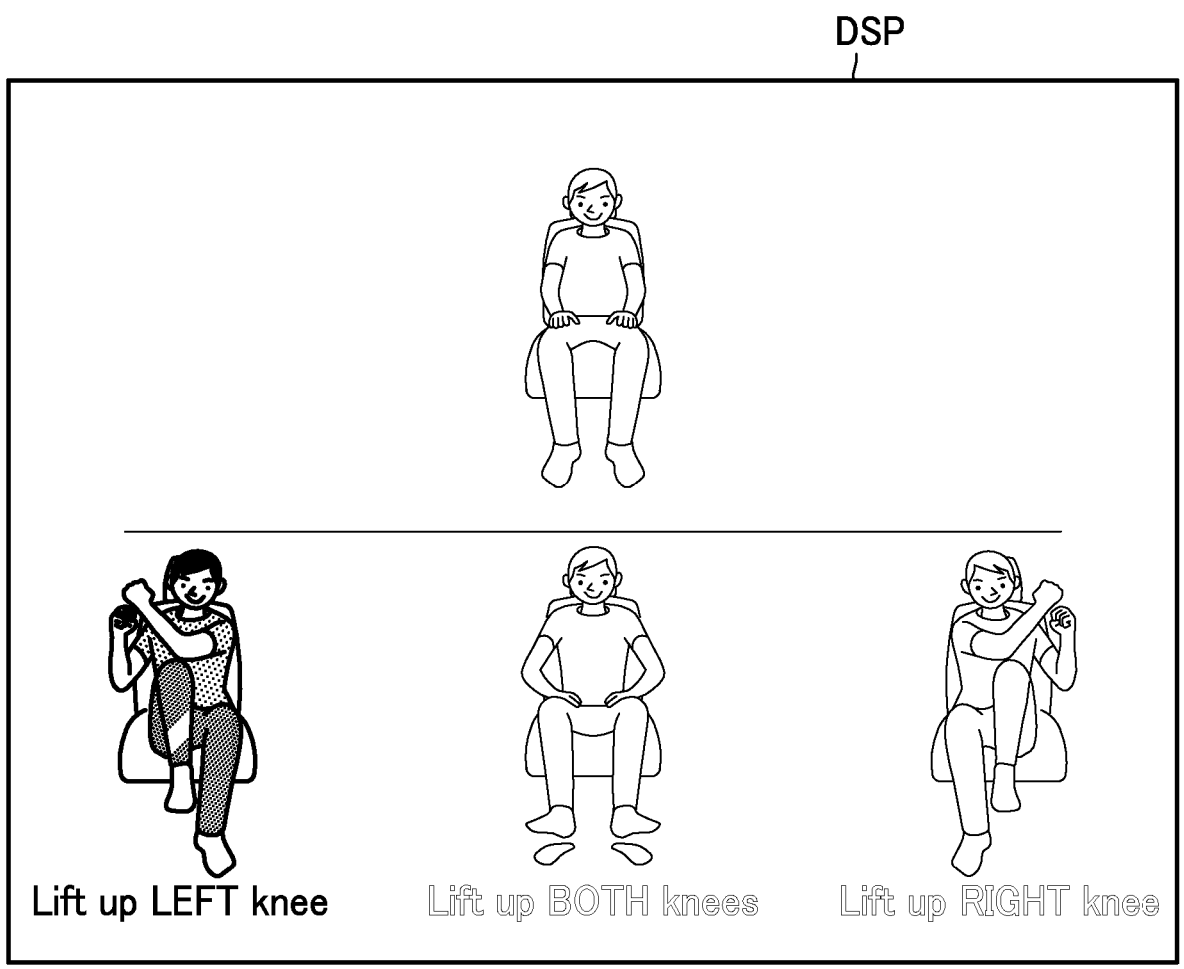
FIG. 6 is a diagram showing a screen for instruction to make a left-knee-lift-up motion.
Figure 7:
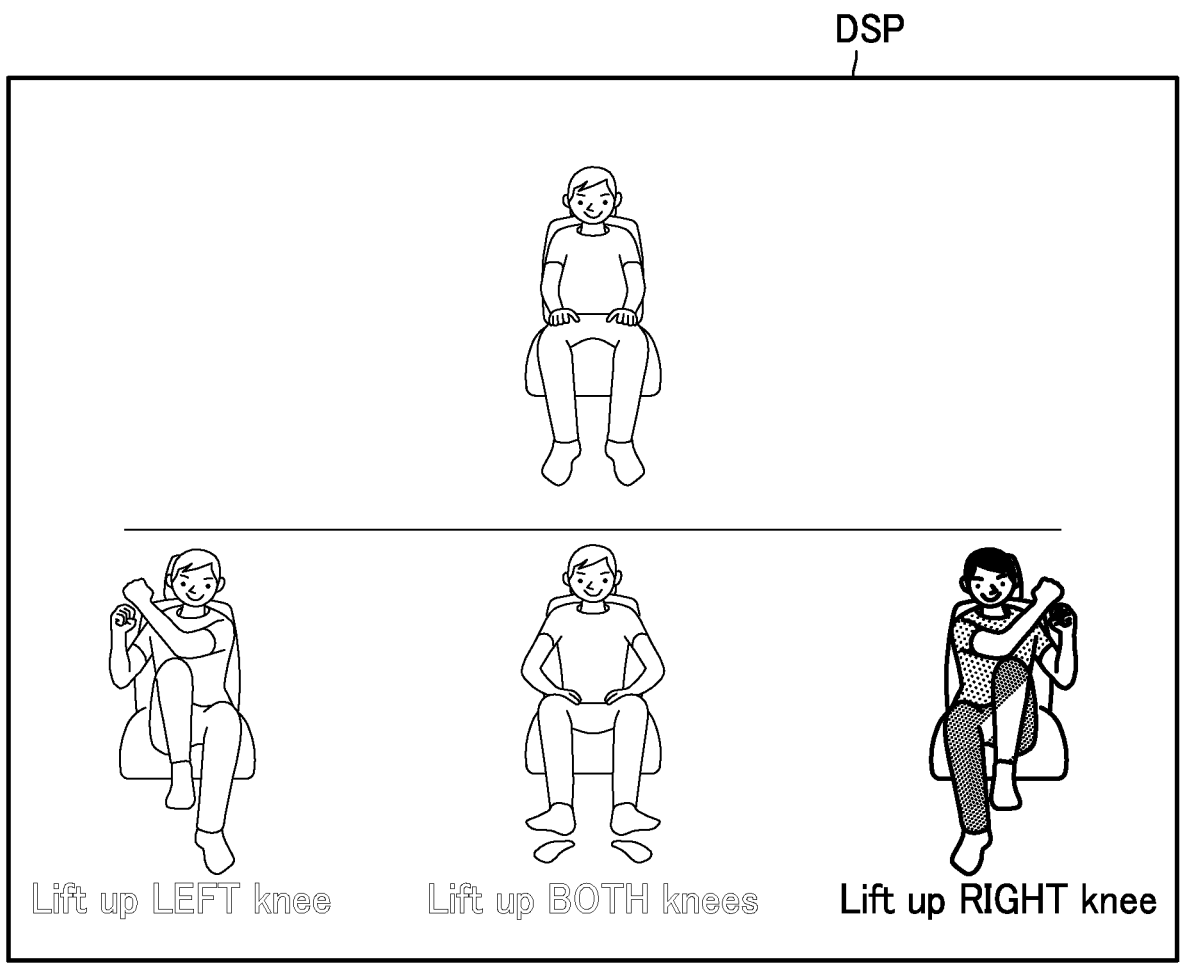
FIG. 7 is a diagram showing a screen for instruction to make a right-knee-lift-up motion.

In this embodiment, as the instruction to prompt an occupant to make a predetermined motion, the smartphone SP outputs to the occupant a first instruction to make a both-knee-lift-up motion as shown in FIG. 5, a second instruction to make a left-knee-lift-up motion as shown in FIG. 6, or a third instruction to make a right-knee-lift-up motion as shown in FIG. 7, as chosen randomly by use of random digits. Herein, the character making a left-knee-lift up motion or a right-knee-lift-up motion shown in each of the screens of FIG. 6 and FIG. 7 is given as a mirror image of an occupant, which is easy for the occupant to follow. It is to be understood that each of the instructions may be given by voice and/or sound outputted from a speaker of the smartphone SP, in addition to images shown on the display DSP.

The smartphone SP has a function of making, after outputting an instruction, a determination based on a change in measurement values (pressure) acquired from the pressure sensor(s) corresponding to the instruction, as to whether or not the occupant has made the predetermined motion. To be more specific, if the instruction chosen is the first instruction, the smartphone SP then acquires a measurement value from the pressure sensor 21L located under the buttock of the occupant.

If the instruction chosen is the second instruction, the smartphone SP then acquires a measurement value from the pressure sensor 23L located under the left thigh of the occupant. If the instruction chosen is the third instruction, the smartphone SP then acquires a measurement value from the pressure sensor 23R located under the right thigh of the occupant.

When the occupant makes a both-knee-lift-up motion in response to the first instruction, the measurement value varying as shown in FIG. 8(a) is acquired from the pressure sensor 21L. The smartphone SP computes a differentiated value as shown in FIG. 8(b) based on the measurement value acquired from the pressure sensor 21L, compares this differentiated value with a third threshold TH3 and a threshold TH11, and thereby makes determinations as to when to output the first instruction and whether the occupant has made the predetermined motion.

To be more specific, the smartphone SP outputs an instruction (first instruction) to prompt an occupant to make a predetermined motion (at time t1) on condition that the differentiated value of the measurement value acquired from the pressure sensor 21L has become smaller than the third threshold TH3. In order to evaluate the occupant's reflexes precisely in this operation, it is desirable that the occupant stays almost still before starting the predetermined motion. Therefore, the third threshold TH3 may be a value close to zero, and an instruction as chosen randomly by use of random digits is outputted upon expiry of a time period as determined on the basis of random digits after the differentiated value has become smaller than this third threshold TH3, so that the occupant's reflexes can be evaluated precisely.

The smartphone SP, after outputting the instruction, determines that the predetermined motion has been started (at time t2), on condition that the differentiated value has crossed the threshold TH11. The smartphone SP determines that the predetermined motion has been completed (at time t3), on condition that the differentiated value has crossed the threshold TH11, and then become smaller than the threshold TH11.

Herein, the threshold TH11 corresponds to the first threshold and the second threshold. In other words, in the present embodiment, the first threshold and the second threshold are the same value (threshold TH11).

The smartphone SP has a function of computing a response time T1 elapsed between outputting the instruction and making the predetermined motion.

In the present embodiment, the response time T1 includes a reaction time T11 elapsed between outputting the instruction to make the predetermined motion and starting the predetermined motion, and a motion completion time T13 elapsed between outputting the instruction to make the predetermined motion and completion of the predetermined motion. Further, in the present invention, the smartphone SP computes a motion time T12 elapsed between starting the predetermined motion and completion of the predetermined motion, other than the reaction time T11 and the motion completion time T13.

When the occupant makes a left-knee-lift-up motion in response to the second instruction, the measurement value varying as shown in FIG. 9(a) is acquired from the pressure sensor 23L. The smartphone SP computes a differentiated value as shown in FIG. 9(b) based on the measurement value acquired from the pressure sensor 23L, compares this differentiated value with thresholds TH3, TH12, and thereby makes determinations as to when to output the second instruction and whether the occupant has made a predetermined motion.

Determination based on the third threshold TH3 as to when to output the second instruction may be made in a manner similar to the aforementioned manner in which determination is made as to when to output the first instruction.

The threshold TH12 corresponds to the first threshold and the second threshold. The threshold TH12 is a threshold for a differentiated value of the measurement value acquired when the left-knee-lift-up motion is made, and takes on a value different from the threshold H11 for use in determination made when the both-knee-lift-up motion is made. It is to be understood that the threshold TH12 is shown in the negative region in FIG. 9(b), for the sake of convenience, but the threshold TH12 assumes a positive value.

The smartphone SP, after outputting an instruction (at time t11), determines that the predetermined motion has been started (at time t12), on condition that the differentiated value is a negative value and the magnitude of the differentiated value has crossed the threshold TH12. The smartphone SP determines that the predetermined motion has been completed (at time t13), on condition that the magnitude of the differentiated value has crossed the threshold TH12, and then the magnitude of the differentiated value has become smaller than the threshold TH12.

Computation of the reaction time T11, the motion time T12, and the motion completion time T13 may be performed in a manner similar to the aforementioned manner in which computation is performed when the both-knee-lift-up motion is instructed.

When the occupant makes a right-knee-lift-up motion in response to the third instruction, the measurement value varying as shown in FIG. 10(a) is acquired from the pressure sensor 23R. The smartphone SP computes a differentiated value as shown in FIG. 10(b) based on the measurement value acquired from the pressure sensor 23R, compares this differentiated value with thresholds TH3, TH13, and thereby makes determinations as to when to output the third instruction and whether the occupant has made a predetermined motion.

The threshold TH13 herein corresponds to the first threshold and the second threshold. In the present embodiment, the threshold TH13 takes on the same value as threshold TH12 mentioned above. Determination made as to when to output the third instruction (time t21), determination made that the predetermined motion has been started (time t22), determination made that the predetermined motion has been completed (time t23), and computation of times T11 to T13 are implemented in the same manners as those implemented when the second instruction is to be outputted.

The smartphone SP has a function of executing a plurality of rounds of a process comprising outputting instructions to make predetermined motions and computing the times T11 to T13, to notify an occupant of averages of the times T11 to T13 acquired in the plurality of rounds, and notifying the occupant of the result of evaluation (hereinafter referred to as "performance level") performed based on the averages of the times T11 to T13. The smartphone SP also has a function of notifying the best times for the acquired times T11 to T13, and notifying the occupant of the performance levels determined based on the best times. To be more specific, as shown in FIG. 11, the smartphone SP shows on the display DSP, and notifies the occupant of, the best times and averages of the times T11 to T13, and performance levels.

The smartphone SP is configured to determine the performance level by comparison made between the reaction time(s) T11 as computed and a reference reaction time T21 as stored. Specifically, the smartphone SP determines the performance level of the average of the reaction times T11 by comparison made between the average of the reaction times T11 computed and the reference reaction time T21. Further, the smartphone SP determines the performance level of the best times of the reaction times T11 by comparison made between the best times of the reaction times T11 computed and the reference reaction time T21. It is to be understood that the reference reaction time T21 with which the average is compared and the reference reaction time T21 with which the best times are compared may assume the same value or assume values different from each other.

To be more specific, the shorter the reaction times T11 (average, best times) computed than the reference reaction time T21 (average, best time), the higher the performance level determined by the smartphone SP is, and the longer, the lower performance level. In the present embodiment, the performance levels are exemplified by three-grade performance levels of high, normal, and low. The performance level is labelled, in descending order, as: "Excellent", "Good", and "Bad".

The smartphone SP chooses the performance level "Excellent", if T11−T21<−α1, "Good", if −α1≤T11−T21≤α2, and "Bad", if T11−T21>α2. Here, α1 and α2 are positive values.

The smartphone SP may be configured to determine the performance levels for the motion time T12 and the motion completion time T13 by comparison made with the reference motion time T22 and the reference motion completion time T23, in a manner similar to that adopted when the reaction time T11 is evaluated.

The smartphone SP has occupant's attributes, e.g., sex, age, etc., recorded therein, and has a function of transmitting the times T11 to T13 as computed and the occupant's attributes to the server SV. The server SV has a function of accumulating the occupant's attributes and the times T11 to T13.

Next, the operation of the smartphone SP (particularly, of the processor in the smartphone SP) is described in detail below.

Figure 2:
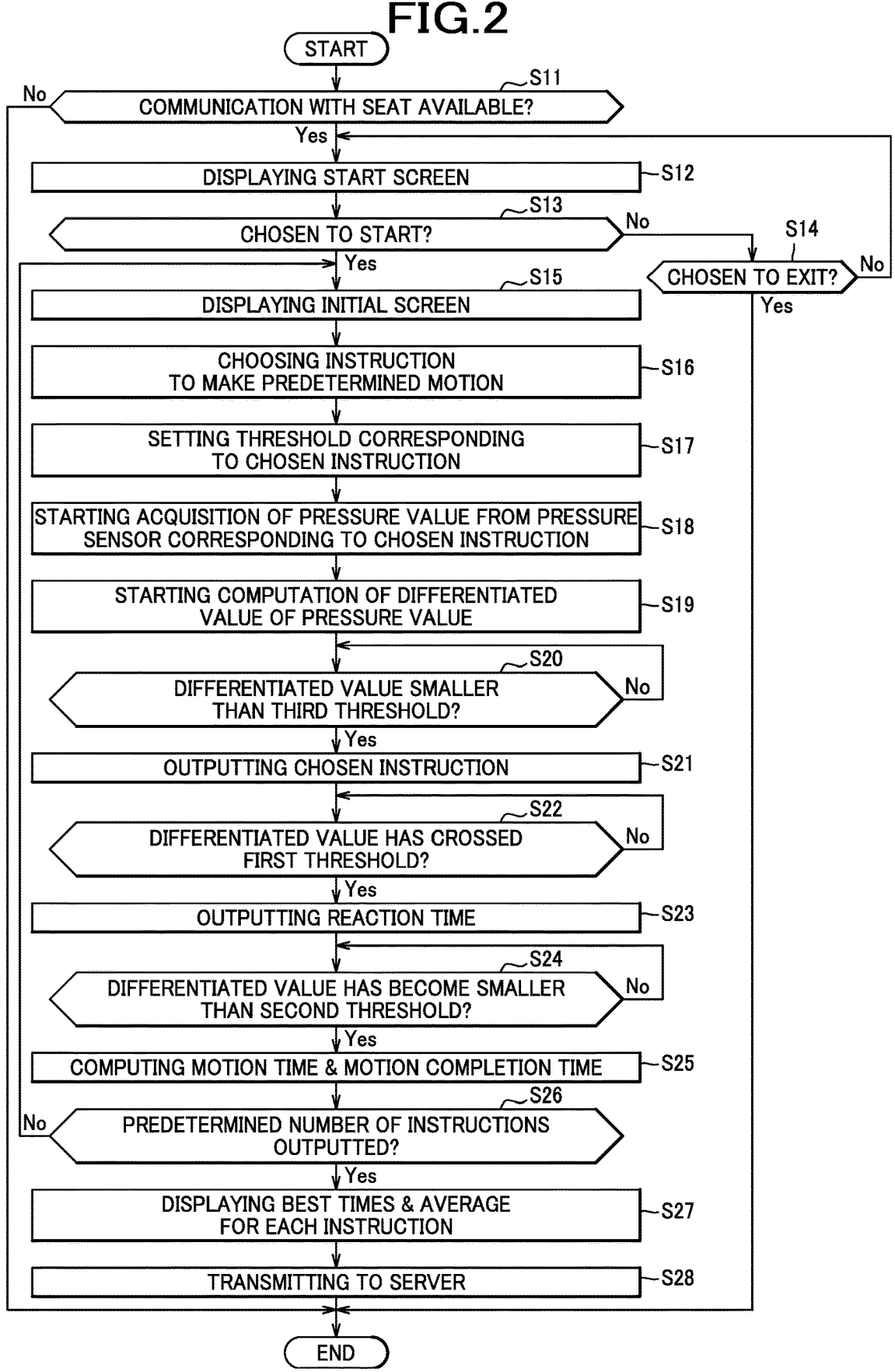
FIG. 2 is a flowchart showing a process in a smartphone.

When an occupant P launches an app for playing a reflexes measurement game, the smartphone SP starts the process shown in FIG. 2 (START). In this process, first, the smartphone SP makes a determination as to whether or not communication with the seat S is available (S11).

If it is determined in step S11 that the communication is not available (No), then the smartphone SP brings the process to an end. If it is determined in step S11 that the communication is available (Yes), then the smartphone SP shows a start screen for the reflexes measurement game (see FIG. 3) on the display DSP (S12).

Figure 3:
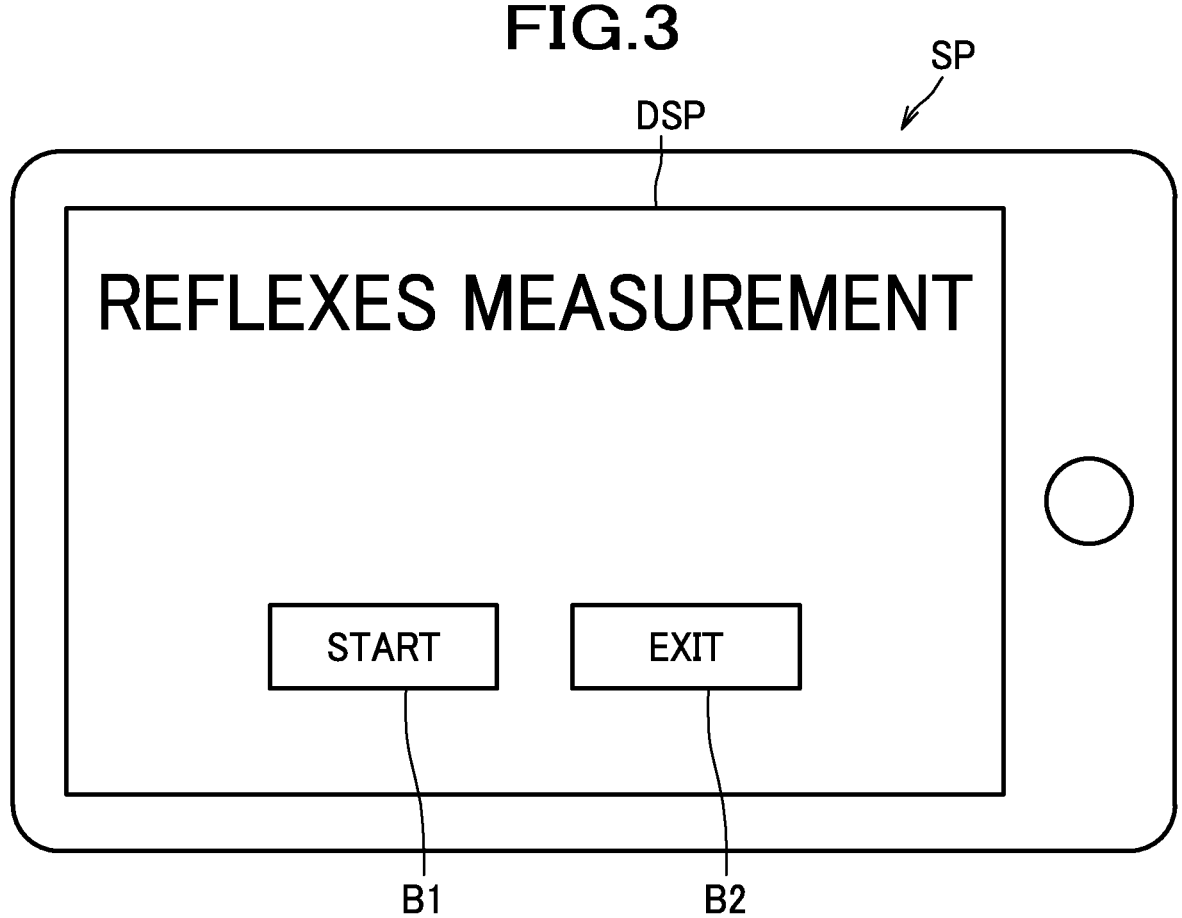
FIG. 3 is a diagram showing a start screen.

In the start screen shown in FIG. 3, a start button B1 for starting the reflexes measurement game and an exit button B2 for exiting the reflexes measurement game are shown.

After step S12, the smartphone SP makes a determination as to whether or not the start button B1 has been chosen (S13). If it is determined in step S13 that the start button B1 has not been chosen (No), then the smartphone SP makes a determination as to whether or not the exit button B2 has been chosen (S14).

If it is determined in step S14 that the exit button B2 has not been chosen (No), then the smartphone SP goes back to the process in step S12. If it is determined in step S14 that the exit button B2 has been chosen (Yes), then the smartphone SP brings the process to an end.

If it is determined in step S13 that the start button B1 has been chosen (Yes), then the smartphone SP shows an initial screen shown in FIG. 4 (S15). In the initial screen, a reference posture to be assumed initially by an occupant is displayed by use of a picture image consisting of the seat and the character, and a message. Specifically, in the initial screen, the character seated back in the seat is shown in color to give it prominence, and a message appears reading "Sit back in the seat, with your back resting on the backrest". With this showing, the occupant can be made intent on assuming the reference posture of sitting back in the seat.

Also in the initial screen, three picture images and three messages showing what the target motions the occupant will be prompted to make from the reference posture are like are displayed in thin lines or gray color to make them inconspicuous. Specifically, in the initial screen, a character who is making a left-knee-lift-up motion is shown along with a message reading "Lift up LEFT knee".

Similarly, a character and a message for the both-knee-lift-up motion, and a character and a message for a right-knee-lift-up motion are shown in the initial screen. Also shown in the initial screen is a message for prompting the occupant to get ready for the motion, reading "Once your posture gets steady, one posture will be shown. Now concentrate on the screen".

The three images corresponding to the three motions are arranged from side to side under the image showing the reference posture. The image corresponding to the both-knee-lift-up motion is arranged in the middle of the three images. The image corresponding to the left-knee-lift-up motion is located on the left of the image corresponding to the both-knee-lift-up motion. The image corresponding to the right-knee-lift-up motion is located on the right of the image corresponding to the both-knee-lift-up motion.

Referring back to FIG. 2, after displaying the initial screen in step S15, the smartphone SP proceeds to randomly choose an instruction to make a predetermined motion (S16). To be more specific, the smartphone SP chooses one instruction randomly from among the first instruction to make a both-knee-lift-up motion, the second instruction to make a left-knee-lift-up motion, and the third instruction to make a right-knee-lift-up motion.

After step S16, the smartphone SP sets a threshold corresponding to the chosen instruction, as a criterial threshold for testing the predetermined motion (S17). Specifically, for example, if the first instruction is chosen as the instruction to make the predetermined motion, the smartphone SP sets a threshold TH11 (see FIG. 8(b)) in step S17.

After step S17, the smartphone SP starts acquiring a measurement value from a pressure sensor corresponding to the instruction (S18). To be more specific, for example, when the smartphone SP has chosen the first instruction as an instruction to make a predetermined motion, the smartphone SP starts acquiring a measurement value from the pressure sensor 21L corresponding to the buttock in step S18. The step S18 corresponds to the acquisition step.

After step S18, the smartphone SP starts computing a differentiated value of the acquired measurement value (S19). After step S19, the smartphone SP makes a determination as to whether or not the differentiated value is smaller than the third threshold TH3 (S20).

If it is determined in step S20 that the differentiated value is smaller than the third threshold TH3 (Yes), then the smartphone SP determines that the occupant stays still in the reference posture, and thereafter, outputs the chosen instruction upon expiry of a time period as determined on the basis of random digits (S21). The steps S20, S21 mentioned above correspond to the instruction step.

Specifically, in step S21 of outputting an instruction, the smartphone SP shows a screen corresponding to the instruction (FIG. 5 to FIG. 7) on the display DSP. As shown in FIG. 5, the screen corresponding to the first instruction displays the character and message corresponding to the both-knee-lift-up motion so prominently as to stand out clearly from other images by coloring, line thickness, etc. As shown in FIG. 6, the screen corresponding to the second instruction displays the character and message corresponding to the left-knee-lift-up motion so prominently as to stand out clearly from other images by coloring, line thickness, etc. As shown in FIG. 7, the screen corresponding to the third instruction displays the character and message corresponding to the right-knee-lift-up motion so prominently as to stand out clearly from other images by coloring, line thickness, etc.

Referring back to FIG. 2, after step S21, the smartphone SP makes a determination as to whether or not the differentiated value has crossed the first threshold, for determination as to whether or not the occupant has started the predetermined motion (S22). To be more specific, for example, when the chosen instruction is the first instruction, the smartphone SP makes a determination as to whether the differentiated value has crossed the threshold TH11 corresponding to the first instruction.

If it is determined in step S22 that the differentiated value has crossed the first threshold (Yes), then the smartphone SP computes a reaction time T11 elapsed between outputting the instruction and starting the predetermined motion (S23). After step S23, the smartphone SP makes a determination as to whether or not the differentiated value has become smaller than the second threshold, for determination as to whether or not the predetermined motion made by the occupant has been completed (S24).

To be more specific, for example, when the chosen instruction is the first instruction, the smartphone SP makes a determination as to whether or not the differentiated value has become smaller than the threshold TH11 corresponding to the first instruction. The steps S22, S24 mentioned above correspond to the determination step.

If it is determined in step S24 that the differentiated value has become smaller than the second threshold (Yes), then the smartphone SP computes the motion time T12 elapsed between starting the predetermined motion and completion of the predetermined motion, and the motion completion time T13 elapsed between outputting the instruction to make the predetermined motion and completion of the predetermined motion (S25). It is to be understood that computations of the motion time T12 and the motion completion time T13 may be performed in this order or vice versa. To be more specific, the motion time T12 may be computed first, and the motion completion time T13 may be computed by adding the motion time T12 to the reaction time T11; alternatively, the motion completion time T13 may be computed first, and the motion time T12 may be computed by subtracting the reaction time T11 from the motion completion time T13.

After step S25, the smartphone SP makes a determination as to whether or not a predetermined number of instructions to make the predetermined motion have been outputted (S26). Herein, the predetermined number may be set arbitrarily; in this embodiment, the predetermined number is six.

If it is determined in step S26 that the predetermined number of instructions have not been outputted (No), then the smartphone SP goes back to the process step S15. If it is determined in step S26 that the predetermined number of instructions have been outputted (Yes), then the smartphone SP shows the best time and the average of each of the times T11 to T13 for the first instruction, the best time and the average of each of the times T11 to T13 for the second instruction, and the best time and the average of each of the times T11 to T13 for the third instruction, on the display DSP, to notify the occupant thereof (S27: see FIG. 11). Further in step S27, the smartphone SP shows a performance level for each instruction on the display DSP, to notify the occupant thereof (see FIG. 11). The step S27 corresponds to the notification step.

After step S27, the smartphone SP transmits the times T11 to T13 for each instruction as computed, together with the occupant's attributes, to the server SV, and brings this process to an end.

Next, a detailed description will be given of one example of a specific operation of the seat system 1.

In a state as shown in FIG. 1, where the communication capability of each of the components (S, SP) constituting the seat system 1 is enabled, when an occupant operates the smartphone SP and launches the reflexes measurement app, the process steps S11 (Yes) to S12 are executed sequentially in the process shown in FIG. 2. As a result, the start screen shown in FIG. 3 is shown on the display DSP.

If the occupant chooses the start button B1, the process steps S13 (Yes) to S15 are executed sequentially. Accordingly, the initial screen shown in FIG. 4 is shown on the display DSP. The occupant, following the guidance of the initial screen, assumes the reference posture of sitting back in the seat S with his/her back resting on the backrest, and waits for an instruction while keeping this posture.

While the occupant is waiting for an instruction, the smartphone SP first chooses one instruction randomly from among three instructions (S16). Assume that the instruction chosen at the outset here is the second instruction.

Having chosen the second instruction, the smartphone SP executes the process steps S17 to S19 sequentially to set the threshold TH12 corresponding to the second instruction (see FIG. 9(b)), acquires a measurement value from the pressure sensor 23L corresponding to the second instruction (left thigh), and computes a differentiated value of the measurement value. If the occupant keeps the reference posture while the smartphone SP is executing the process step S20, the differentiated value is smaller than the third threshold TH3 (at time t11) as shown in FIG. 9(b); therefore, the smartphone SP makes a determination in the affirmative (Yes) in step S20, and outputs the chosen second instruction (S21, at time t11).

Accordingly, the showing on the display DSP changes from the initial screen to the screen shown in FIG. 6; in response, the occupant tries to follow the screen of FIG. 6 and proceeds to make a left-knee-lift-up motion. According to this motion, the measurement value of the pressure sensor 23L corresponding to the left thigh changes as shown in FIG. 9(a), and the differentiated value of the measurement value changes as shown in FIG. 9(b).

If the smartphone SP determines that the differentiated value is negative and the magnitude of the differentiated value has crossed the threshold TH12 (Yes, in step S22), then the smartphone SP computes the reaction time T11 for the left-knee-lift-up motion (S23). Thereafter, if the smartphone SP determines that the magnitude of the differentiated value has become smaller than the threshold TH12 (Yes, in step S24), then the smartphone SP computes the motion time T12 and the motion completion time T13 for the left-knee-lift-up motion (S25).

Subsequently, the smartphone SP determines in step S26 that a predetermined number (six) of instructions have not been outputted (No), and brings the process to step S15. As a result, the showing on the display DSP returns from the screen of FIG. 6 back to the initial screen again. In response, the occupant tries to follow the initial screen, assumes the reference posture again, and waits for the next instruction.

Thereafter, if the instructions are sequentially chosen, for example, the first instruction, the third instruction, the third instruction, the second instruction, and the first instruction are chosen in this sequence, and the process steps S15 to S26 are repeated five times, then the smartphone SP makes a determination in the affirmative (Yes) in step S26, and shows the screen as in FIG. 11 on the display DSP. Accordingly, the occupant can be informed of the best times and average of each time T11 to T13 for the left-knee-lift-up motion, the both-knee-lift-up motion and the right-knee-lift-up motion. Further, the occupant can be informed of the performance level for each motion.

With the seat system 1 in the present embodiment, the following advantageous effects can be achieved.

When an occupant seated on the seat S has made a predetermined motion in accordance with an instruction from the smartphone SP, the smartphone SP notifies the occupant of a response time T1 elapsed between outputting the instruction and making the predetermined motion, and other information based on the measurement value(s) acquired from the pressure sensor(s). Accordingly, the occupant seated on the seat S can grasp his/her own reflexes.

Since the response time T1 includes both of the reaction time T11 and the motion completion time T13, the occupant's reflexes can be adequately quantified.

Since the smartphone SP determines the performance level by comparison made between the response time T11 as computed and the reference response time T21 as stored, the occupant can know the level of his/her reflexes or ability to react quickly, from the performance level.

Since the motion of the occupant is evaluated based on the pressure value (particularly, its differentiated value) acquired from the pressure sensor, the occupant's motion can be determined adequately.

Since the instruction is outputted on condition that the differentiated value has become smaller than the third threshold TH3, the instruction to make a predetermined motion is given when the occupant stays almost still in the reference posture; therefore, the reflexes can be determined precisely.

With this configuration, the occupant can be instructed to make randomly chosen different motions; therefore, the occupant can be notified of his/her reflexes for the respective motions. Furthermore, the occupant can grasp his/her own aptitude, which is a motion he/she is good at and which is a motion he/she is poor at.

Since a plurality of rounds of a process comprising outputting the instruction and computing the times T11 to T13 are executed and the occupant is notified of the averages of the times T11 to T13, the occupant can know the averages of his/her reflexes.

Since the attributes and the response times (times T11 to T13) for occupants are accumulated in the server SV, the response time for an occupant can be compared, for example, with the response times for others having the same attributes as the attribute of the occupant.

Although the first embodiment has been described above, it should be appreciated that the present embodiment is an example of illustrative, non-limiting embodiments, and can be modified where appropriate for practical application, as in the other embodiments which will be described below. In the following description, elements having substantially the same configurations as those of the first embodiment will be designated by the same reference characters, and a description thereof will be omitted.

In the above-described embodiment, the occupant is notified of the both of the response time and the performance level; instead, the occupant may be notified of the response time only, or the occupant may be notified of the performance level only.

In the above-described embodiment, the both of the reaction time T11 and the motion completion time T13 are adopted as a response time to be provided for notification; however, the response time for notification may include at least one of the reaction time and the motion completion time.

In the above-described embodiment, the first threshold and the second threshold have the same value; however, the first threshold and the second threshold may have different values. For example, the second threshold may be a value smaller than the first threshold. Although the first threshold and the second threshold are set at a value different from one instruction to another, the first threshold and the second threshold for the second instruction may be the same value as of the first threshold and the second threshold for the third instruction.

In the above-described embodiment, the pressure sensor corresponding to the first instruction is one pressure sensor 21L located under the buttock of an occupant, but may instead be four pressure sensors 21L, 21R, 22L, 22R located under the buttocks of the occupant. In this configuration, the smartphone SP may be configured to output the first instruction, for example, on condition that all or the average of the differentiated values of the four pressure values are/is smaller than the third threshold TH3. Alternatively, the smartphone SP may be configured to determine that the occupant has started a predetermined motion, if one of the four differentiated values has crossed the threshold TH11 corresponding to the first instruction. Furthermore, the smartphone SP may be configured to determine that the predetermined motion has been completed, if it is determined that the predetermined motion has been started and then all of the four differentiated values have become smaller than the threshold TH11 corresponding to the first instruction.

In the above-described embodiment, the seat S is illustrated as a vehicle seat, but the seat may be a seat installed in a facility such as a hospital or the like, instead. When the seat S is installed in a hospital, the seat S can be utilized effectively because the seat S can be used for rehabilitation of patients.

More specifically, a therapist who gives advice to a patient necessary to undergo rehabilitation can quantitatively check the reflexes of the patient as measured in the seat S, on the display DSP of the smartphone SP. Accordingly, variations among individual therapists can be leveled out. Moreover, the therapist can check on the display the occupant's recovery level, based on the occupant's reflexes measured in the seat S. Furthermore, from the numerical representation of the response times or the like as quantified responsivity for each motion, as shown in FIG. 11, the therapist can check whether or not the occupant has made a proper motion.

The smartphone SP may also be configured to make a notification of admonition to the occupant when the performance of the reflexes measurement is worse than usual. For example, when the best time as recorded in this round for the right-knee-lift-up motion as shown in FIG. 11 is much worse than the normal best time (e.g., an average of the best times for several tens of rounds of trial in the past), the smartphone SP may notify the occupant of a message of admonition, saying "Right leg's response speed is unusually slow; so, checkup at the hospital is advisable".

In this configuration, the smartphone may further be configured to present a proposal for a corrective physical exercise, an advertisement, a hospital, a lifestyle modification plan, etc.

The smartphone SP may also be configured such that a target figure of the response time or the like is displayed in the screen, and once the target is reached, the occupant can earn reward points. The reward points may be configured as points which can be redeemed for shopping or the like. The smartphone SP may also be configured such that if a predetermined number of points are amassed, information (a tip) fit for the user's preferences is presented.

The reflexes measurement game may be utilized as elder driver's driving competency testing, or in readiness-to-drive testing to be carried out before driving.

Deviation from each motion may be determined automatically. For example, if the differentiated value has not crossed the first threshold even after a lapse of a predetermined time period from outputting the instruction to make the right-knee-lift-up motion, a notification of error using a message, such as "Lift right knee much higher", "Lift right knee a bit higher" or the like, according to the difference between the differentiated value and the first threshold may be given.

A measure of performance for each attribute may be made based on the response times for each attribute accumulated in the server SV.

In the above-described embodiment, the pressure sensors each configured to detect pressure applied on a portion (spot) of the seat surface of the seat S are illustrated as an example; however, the pressure sensor may be a pressure distribution sensor configured to detect distribution of pressure applied on an entire area of the seat surface. The smartphone SP may be configured to make a determination based on the distribution of pressure as to whether or not the occupant has made a proper motion. Alternatively, the pressure sensors as in the above-described embodiment may be provided on the pressure distribution sensor.

The sensor may not be limited to a pressure sensor, but may be an optical sensor, sound/voice detection sensor, a position detection sensor, a capacitance sensor, or the like. When the optical sensor or the capacitance sensor is used, the predetermined motion may be a motion of placing a hand in a position of detection by the sensor and removing the hand from the position. When the sound/voice detection sensor is used, the predetermined motion may be a production of voices by the occupant.

The testing of the motion may be done on the basis not only of a differentiated value but also of a pressure value.

In the above-described embodiment, the smartphone SP is illustrated as an example of the terminal, but the terminal may be a mobile terminal other than the smartphone SP, such as a tablet. The terminal may be a terminal fixed to the seat or a built-in terminal fitted integrally in the seat. The terminal may be a terminal as a component of a car navigation system.

Any of the elements explained in relation to the exemplified embodiments and illustrative modified examples described above may be implemented in combination as desired.

A second embodiment will be described below in detail with reference made to the drawings where appropriate.

Figure 12:
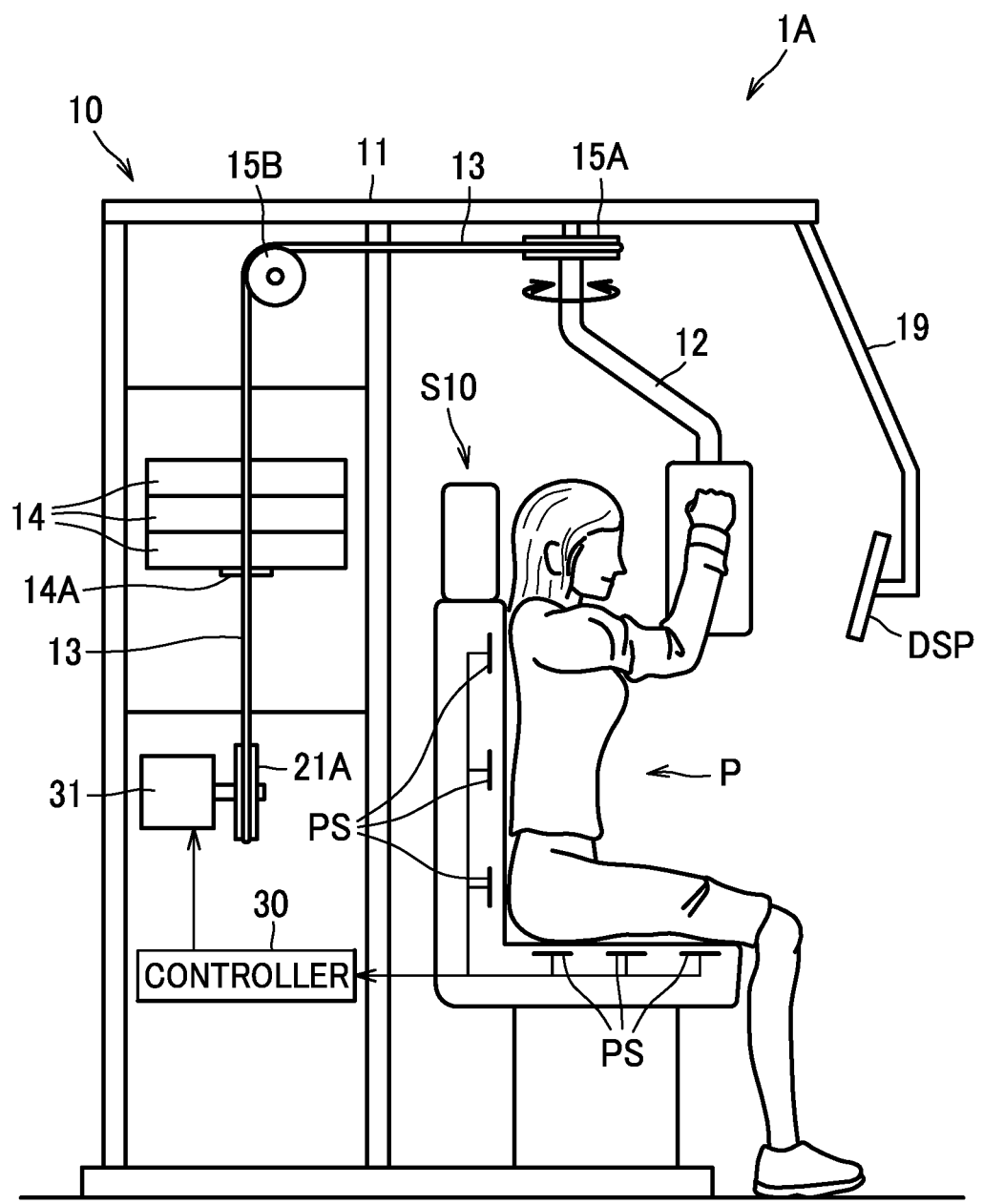
FIG. 12 is a side view of a training seat according to a second embodiment.

As shown in FIG. 12, a training seat 1A of the present embodiment includes a seat body S10, an exercise device 10 provided separably outside of the seat body S10, for a user P to take exercise, and a controller 30.

The training in this description includes both of resistance training for an able-bodied person to build up his/her muscular strength, and rehabilitation for a physically handicapped person incapacitated due to illness, accident, or the like to recover his/her physical ability.

Figure 13:
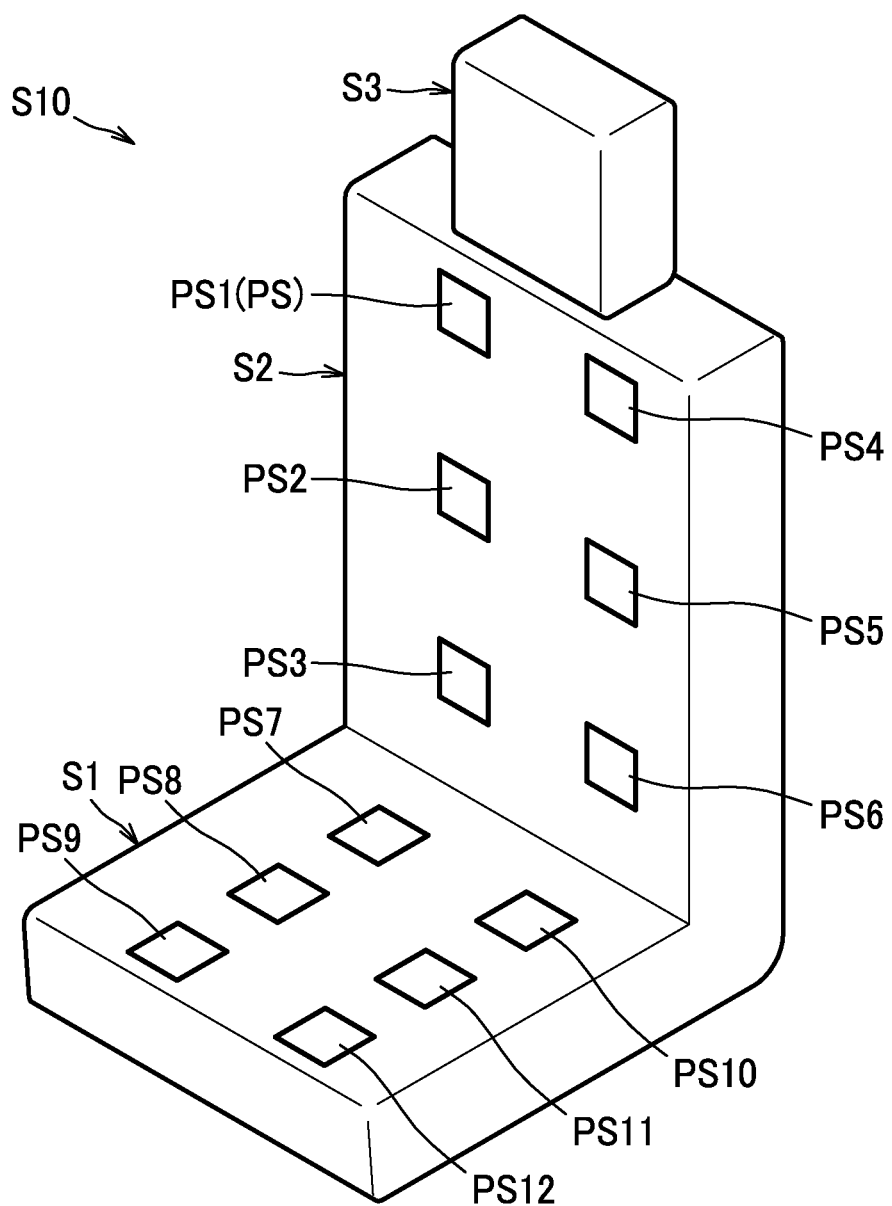
FIG. 13 is a perspective view of a seat body.

The seat body S10 includes, as shown in FIG. 13, a seat bottom S1, a seat back S2, and a headrest S3. The headrest S3 may not be provided, or may be provided integrally with the seat back S2.

The seat bottom S1, the seat back S2, and the headrest S3 are made up of frames (not shown) upholstered with pad made of urethane foam or the like and further covered with outer covering made of fabrics, leather, synthetic leather or the like.

The seat bottom S1 and the seat back S2 include pressure sensors PS (PS1 to PS12) provided as an example of a sensor configured to acquire biological information on a user seated on the seat body S10. The pressure sensors PS are located between the outer covering and the pad.

Six pressure sensors PS, by way of example, are provided in the seat bottom S1 and the seat back S2, respectively. Specifically, the seat back S2 includes a pressure sensor PS1 located in a portion corresponding to the right shoulder, a pressure sensor PS2 located in a portion corresponding to the right back, and a pressure sensor PS3 located in a portion corresponding to the right lumbar region. The pressure sensors PS1, PS2, PS3 are arranged from above to below in this sequence. The seat back S2 also includes pressure sensors PS4, PS5, PS6 located in positions bilaterally symmetric to the pressure sensors PS1, PS2, PS3.

On the other hand, the seat bottom Si includes a pressure sensor PS7 located in a portion corresponding to the right buttock, and pressure sensors PS8, PS9 located in a portion corresponding to the right thigh. The pressure sensors PS7, PS8, PS9 are arranged from the rear to the front in this sequence. The seat bottom S1 also includes pressure sensors PS10, PS11, PS12 located in positions bilaterally symmetric to the pressure sensors PS7, PS8, PS9.

Referring back to FIG. 12, the exercise device 10 is, for example, a butterfly machine for mainly strengthening pectoralis major muscle. The exercise device 10 includes a frame 11, movable parts 12, a wire 13, weights 14, and a resistance generator 31. The seat body S10 is fixed at a front part of the frame 11.

The movable parts 12 are provided at an upper part of the frame 11, rotatably about vertical axes. Two movable parts 12 are provided one at the left and the other at the right, in such positions as fit for a user P to exercise his/her left and right upper arms by opening and closing the movable parts 12 using the upper arms. Each movable part 12 has a sheave 15A to which a wire 13 is fixed, and is configured such that as the movable part 12 rotates 12, the sheave 15A rotates accordingly.

The wire 13 has ends connected to the sheaves 15A and the other end is fixed to the weights 14 and to the resistance generator 31.

To be more specific, at the frame 11, a pulley 15B is provided rearward of the sheaves 15A. The wire 13 is wound around the sheaves 15A, run through the pulley 15B to change its direction by the pulley 15B, and thus directed toward downward. The vertically extending portion of the wire 13 is passed through the weights 14, and a fixing part 14A is provided to thereby fix the wire 13 and the weights 14 together.

The resistance generator 31 is, for example, made of a motor, and has a shieve 21A provided on a portion corresponding to the output shaft of the motor. The end of the wire 13 is fixed to the shieve 21A.

A bracket 19 is attached to a front end of the upper part of the frame 11, and a display DSP is fixed to the bracket 19.

The training seat 1A includes a switch (not shown) for activating the controller 30 in an appropriate position, for example, near the display DSP.

The controller 30 is connected to the pressure sensors PS. The controller 30 is also connected to the resistance generator 31 of the exercise device 10 so that the resistance of the exercise device 10 is made controllable. Further, the controller 30 is connected to the display DSP so that a user P can be notified of the state of exercise, advises or the like.

The controller 30 includes a CPU, a ROM, a RAM, etc., and is configured to be capable of executing a variety of processes by the CPU executing programs stored beforehand in a storage medium (the ROM or the like).

The controller 30 is configured to acquire biological information from the pressure sensors PS, and notify the user P of information related to a state of exercise of the user based on the biological information.

To be more specific, the controller 30 can acquire a heartbeat signal as an example of the biological information from change in pressure detected by the pressure sensor(s) PS, in particular, the pressure sensors PS2, PS5 corresponding to the back of the user P.

The controller 30 controls exercise stress the user P undergoes during training, based on the heart rate N. For example, if the controller 30 determines, based on the heart rate N, that the exercise stress on the user P is smaller than a predetermined reference value N1, the controller 30 then increases the resistance of the exercise device 10. On the other hand, if the controller 30 determines, based on the heart rate N, that the exercise stress on the user P is greater than a predetermined reference value N2, then the controller 30 reduces the resistance of the exercise device 10. The reference value N2 is a value greater than the reference value N1. The exercise stress can be adjusted by the resistance generator 31. The resistance generator 31 has mechanics similar to those of a motor, and thus can generate a resistance, like a regeneration brake, when the wire 13 is let out from the sheave 21A.

When the training is started, the controller 30 causes the resistance generator 31 to generate a resistance. Therefore, from the start of training, a user P takes training under the physical stress the amount of which is the total exercise stress of the weights 14 plus a resistance generated by the resistance generator 31.

Further, the controller 30 outputs pressure values acquired by the pressure sensors PS, as a state of exercise of the user P, in the form of a visual image, on the display DSP. At this time, areas high and low in pressure values are shown distinguishably in hue or saturation (or lightness).

The controller 30 is further configured to evaluate a posture of the user P during exercise by comparing the pressure values with predetermined criteria. For example, the proportion of the magnitudes of the pressure values P1 to P12 acquired from the pressure sensors PS1 to PS12 may be compared with the proportion of the pressure values as acquired when the ideal posture is maintained during exercise for training in the butterfly machine, so that the posture during exercise can be evaluated.

To elaborate on one example of such evaluation, first, in view of the fact that the pressure values P1 to P12 vary greatly with the weight of the user P, the pressure values P1 to P12 are normalized in such a manner that the total equals a predetermined value.

Then, the amount of deviation M of the proportion of the normalized pressure values P1 to P12 from the proportion of the ideal pressure values L1 to L12 is computed. The amount of deviation M may, for example, be computed by:

$$M=(P1-L1)^2+(P2-L2)^2+ \ldots +(P12-L12)^2$$

The controller 30 shows on the display DSP, if it is determined that the amount of deviation M is greater than a threshold Mth, a message indicating that the posture is not good and pointing out which area impairs the right proportion. An area(s) impairing the right proportion may be determined from the magnitude of each term (e.g., $(P1-L1)^2$, etc.) used to compute the amount of deviation M.

Next, a description will be given of an example of a process executed by the controller 30, with reference to FIG. 14.

Figure 14:
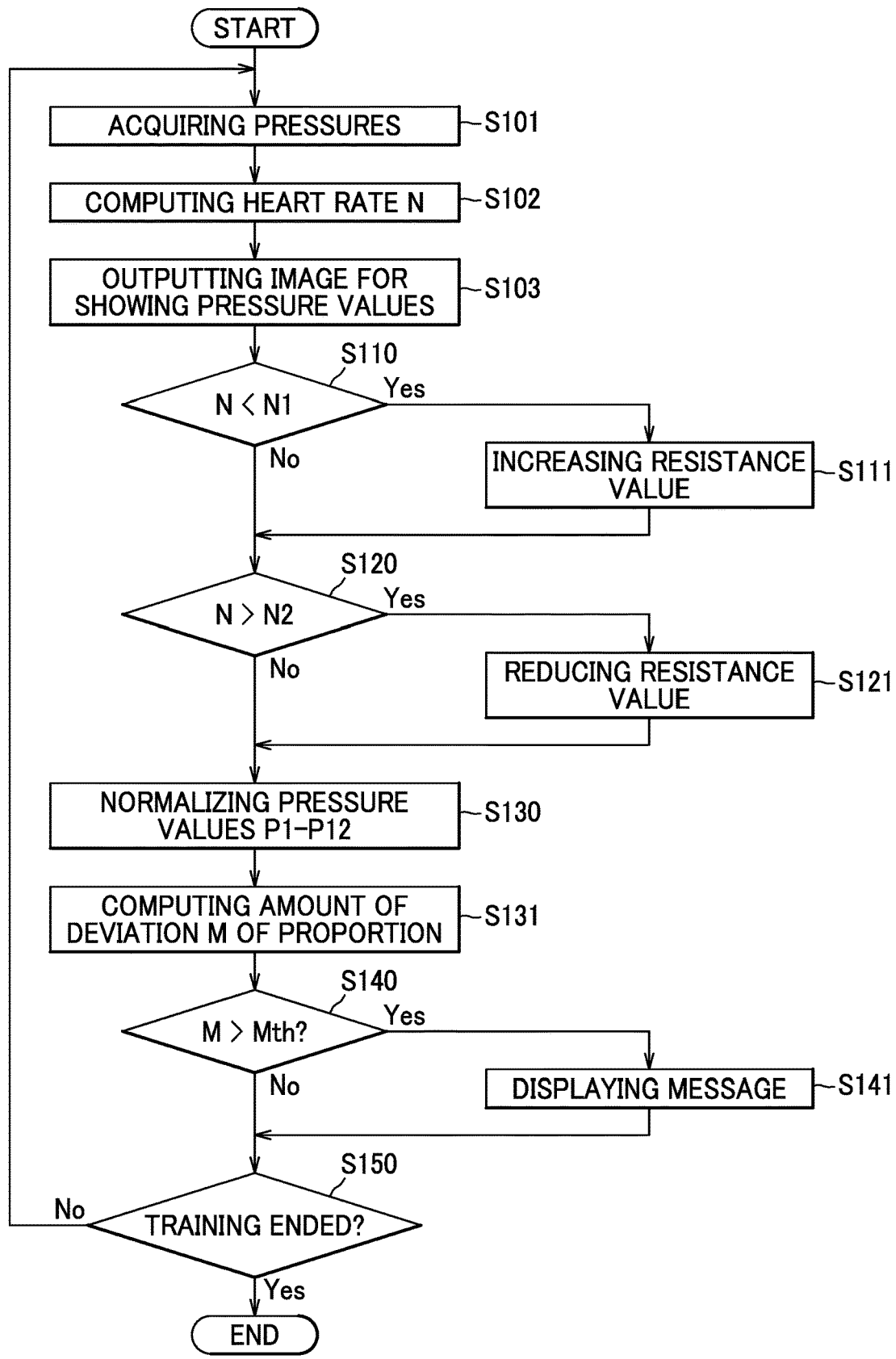
FIG. 14 is a flowchart showing one example of a process of a controller.
Figure 15:
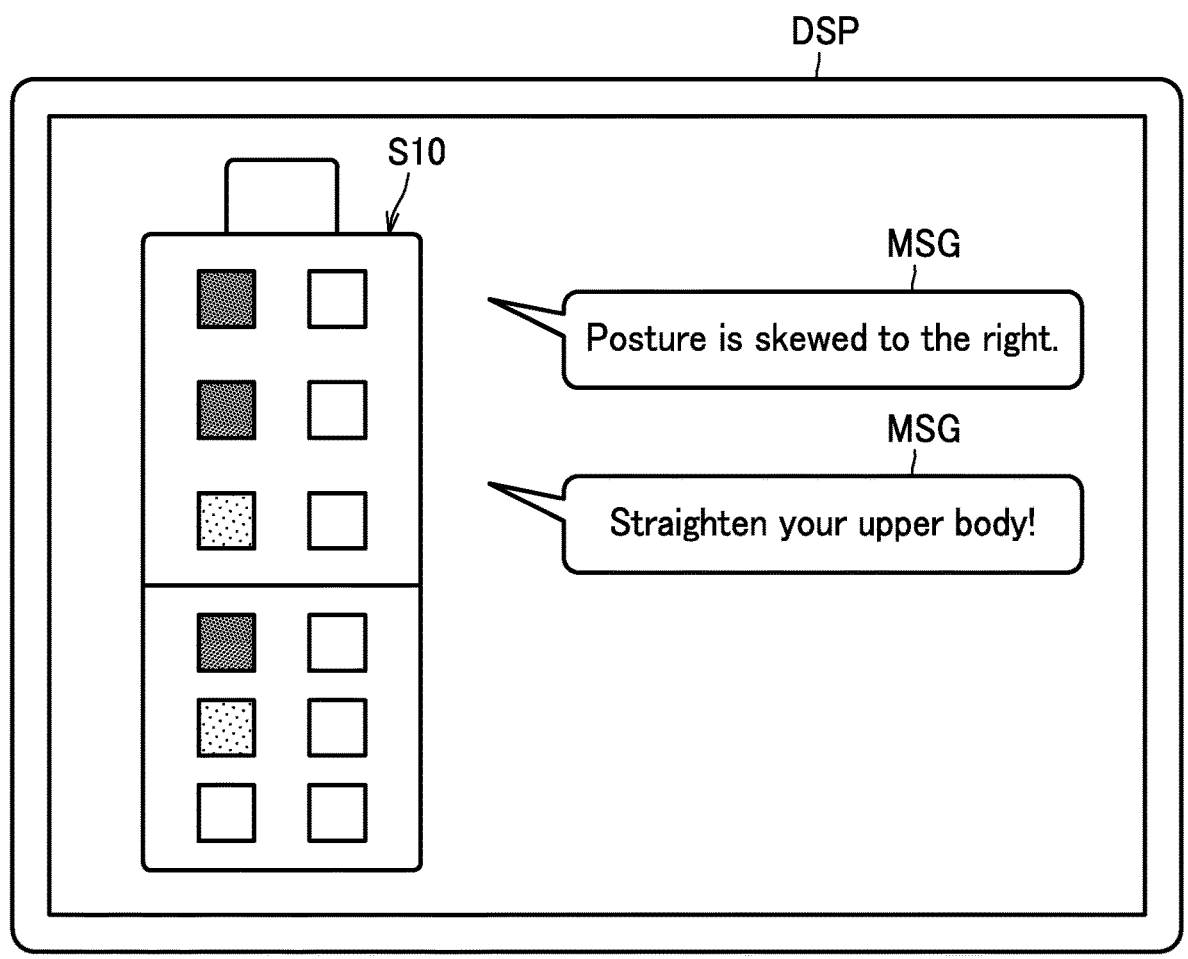
FIG. 15 is a diagram showing a screen displaying the state of pressures and a message.

As shown in FIG. 14, when the training is started by the user P turning on a switch, the controller 30 first acquires pressure values P1 to P12 from the pressure sensors PS1 to PS12 (S101). The controller 30 then computes a heart rate N from changes of pressures acquired from the pressure sensors PS1 to PS12 (S102). The controller 30 then outputs an image for showing the pressure values on the display DSP (S103). For example, as shown in FIG. 15, on the display DSP, an image of the seat body S10 is outputted in which squares filled in with colors having saturation levels varying with the magnitudes of the pressure values are shown in positions corresponding to the pressure sensors PS.

Although not shown in FIG. 14, the controller 30 controls the resistance generator 31 using a resistance value being specified during training.

Next, the controller 30 makes a determination as to whether or not the heart rate N is lower than the reference value N1 (S110), and if lower (Yes, in step S110), then increases a resistance value for use in controlling the resistance generator 31 (S111). The controller 30 does not increase the resistance value if the heart rate N is not lower than the reference value N1 (No, in step S110).

Next, the controller 30 makes a determination as to whether or not the heart rate N is higher than the reference value N2 (S120), and if higher (Yes, in step S120), then reduces the resistance value for use in controlling the resistance generator 31 (S121). The controller 30 does not reduce the resistance value if the heart rate N is not higher than the reference value N2 (No, in step S120).

Next, the controller 30 normalizes the pressure values P1 to P12 (S130). Then, the amount of deviation M of the proportion of the pressure values P1 to P12 is computed (S131), and a determination is made as to whether or not the amount of deviation M is greater than the threshold Mth (S140). If it is determined that the amount of deviation M is greater than the threshold Mth (Yes, in step S140), then the controller 30 shows a message on the display DSP (S141). For example, as in the image of the seat body S10 shown in FIG. 15, when the pressure values lack proportion, i.e., out of balance with the pressure from the right side of the body being too strong, messages MSG illustrated such as "Posture is skewed to the right" and "Extend the upper body straight", etc. may be displayed.

After the messages MSG are displayed or when the determination made is that the amount of deviation M is not greater than the threshold Mth (No, in step S140), the controller 30 then makes a determination, in step S150, as to whether or not the training has been ended (S150), and if the determination indicates that the training has not been ended (No, in S150), then repeats the process starting from step S101, while if the determination indicates that the training has been ended (Yes, in S150), then brings the process to the end.

With the training seat 1A as described above, the following advantageous effects can be achieved.

Since the controller 30 notifies a user P of the pressure value distribution visualized in the form of an image and shown on the display DSP, as information about the state of exercise based on the biological information acquired from the pressure sensors PS, the user P who is taking training can know the state of exercise.

Since the controller 30 controls the resistance of the exercise device 10 based on the biological information acquired from the pressure sensors PS, the user P can take an effective training with a properly-controlled resistance.

Since the pressure sensors for acquiring the biological information on the user are provided at the seat body S10, the user P need not have the sensors attached to his/her body. Therefore, the user P can take training in a relaxed state without concern for the sensors. Thus-obviated necessity of attaching the sensors to the body may ease the user's apprehensions about sanitary conditions.

Since the controller 30 evaluates the posture of the user P during exercise by comparison made with a value (threshold Mth) as a predetermined criterion, and presents the same for notification as messages MSG shown on the display DSP, the user can try to assume a good posture for training.

Although the second embodiment has been described above, it should be appreciated that the present embodiment is an example of illustrative, non-limiting embodiments, and can be modified where appropriate for practical application, as in the other embodiments which will be described below. In the following description, elements having substantially the same configurations as those of the second embodiment will be designated by the same reference characters, and a description thereof will be omitted.

Figure 16:
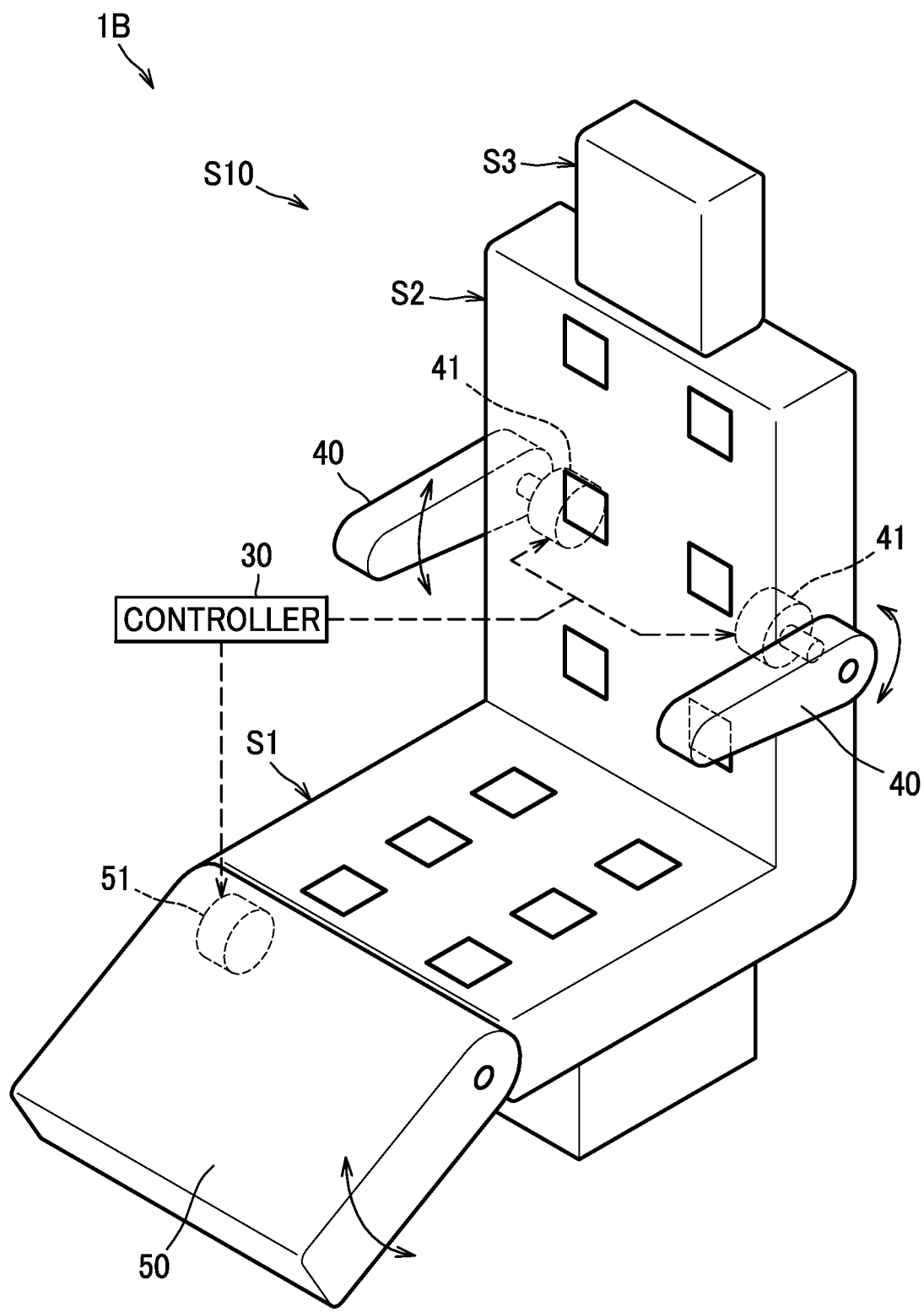
FIG. 16 is a perspective view of a training seat according to a modified example.

For example, the training seat 1A in the second embodiment is configured such that the exercise device 10 is provided separately outside of the seat body S10, but the exercise device may be provided integrally with the seat body S10 as in a training seat 1B shown in FIG. 16. The training seat 1B includes armrests 40, as an example of an exercise device, provided at the left and right of the seat back S2, and includes an ottoman 50, as an example of an exercise device, provided at a front end of the seat bottom S1.

The armrests 40 are rotatably supported on the seat back S2. A resistance generator 41 made of a motor is provided on a pivot of the armrest 40.

The ottoman 50 is rotatably supported on the seat bottom S1. A resistance generator 51 made of a motor is provided on a pivot of the ottoman 50.

The controller 30 is configured to control the resistances generated by the resistance generator 41 and the resistance generator 51.

The thus-configured training seat 1B generates resistances as if to push the armrests 40 upward by the resistance generators 41, so that a user P can take exercise of pushing down the armrests 40 using his/her forearms.

The training seat 1B also generates a resistance as if to push the ottoman 50 upward by the resistance generator 51, so that a user P can take exercise of pushing down the ottoman 50 using his/her lower legs. When a user P takes rehabilitation exercise, it may be used in a reverse manner such that a lower-leg-lift-up exercise of the user P may be supported by the ottoman 50.

Although the second embodiment illustrates a pressure as a signal for acquiring biological information, a temperature or a humidity may be acquired instead. Physical quantities other than the pressure, such as infrared or other kinds of light, may be used to acquire the heart rate of a user P.

Although the second embodiment illustrates a particular configuration in which the controller 30 and the display DSP are separately provided, the controller 30 and the display DSP may be provided as an integral unit. As an example of a combination of the controller 30 and the display DSP, a smartphone or tablet may be used.

Although the second embodiment illustrates, as an example of a state of exercise, the pressure values only, shown on the display DSP, a notification may be given of other values, e.g., heart rates, body temperatures, etc. as the state of exercise.

Although the second embodiment illustrates, as an example of a pressure sensor, individually allocated sensors each configured to acquire a pressure of a corresponding spot, the pressure sensor may be a pressure distribution sensor configured to measure a distribution of pressures.

Although the second embodiment illustrates sensors provided under the outer covering of the seat, i.e., embedded in the seat, the sensor(s) may be provided on the outside of the seat. In this alternative arrangement, the sensors may be provided in positions adjusted to conform to the physique of a user. For example, a user may glue the sensors to proper positions on the seat conformable to his/her own physique. The sensors may be detachably attached to the surface of the seat by the use of hook-and-loop fasteners, or the like.

Although the second embodiment illustrates, as an exercise device, a butterfly machine, any kind of exercise device may be used without limitation. For example, the exercise device may be an exercise bike, or a pedal wheelchair that is a wheelchair with pedals like those of the exercise bike.

Although the second embodiment illustrates the use of the heart rate for evaluating the exercise stress on a user, any lapse into incorrect posture may be detected to evaluate the stress. For example, if the degree of the lapse in posture is smaller, then it is determined that the stress is smaller, while if the degree of the lapse in posture is greater, then it is determined that the stress is greater.

Where the temperature is acquired as the biological information, if the temperature, i.e., the body temperature, is higher, then it is determined that the stress is greater, while if the temperature is lower, then it is determined that the stress is smaller.

Where the humidity is acquired as the biological information, if the humidity, i.e., the perspiration, is higher, then it is determined that the stress is greater, while if the humidity is lower, then it is determined that the stress is smaller.

Data on the state of exercise acquired in the training seat may be accumulated in a server or a terminal owned by a user. By making use of such data of the state of exercise, the physical ability of the user can be determined. For example, when the user takes training in another training seat, the controller of this training seat may import the accumulated data of the state of exercise, and thus can set a resistance given by the resistance generator at a magnitude conformable to the user.

Although the second embodiment illustrates the training seat comprising a seat back, the seat back may not be provided therein.

Although the second embodiment illustrates the notification of the state of exercise as given to a user by showing on the display, the notification may be made by any other means, such as sound, braille, etc.

Any of the elements explained in relation to the exemplified embodiments and illustrative modified examples described above may be implemented in combination as desired.

The invention claimed is:

1. A seat system comprising:
 a seat that comprises a seat body;
 a sensor provided at the seat body and configured to acquire information for use in detecting motion of an occupant seated on the seat body; and
 a terminal configured to acquire the information from the sensor,
 wherein the terminal is configured to:
  output an instruction to prompt the occupant to make a predetermined motion;
  determine a differentiated value of a signal acquired from the sensor;
  determine, based on the information acquired from the sensor, whether or not the occupant has made the predetermined motion;
  determine that the predetermined motion has started based on a magnitude of the differentiated value crossing a first threshold;
  determine that the predetermined motion has been completed based on the magnitude of the differentiated value crossing the first threshold and then decreasing below a second threshold that is not more than the first threshold; and
  notify the occupant of a response time or a performance level evaluated based on the response time or both, the response time comprising at least one time selected from the group consisting of a reaction time elapsed between the outputting of the instruction and the making of the predetermined motion, and a motion completion time elapsed between the outputting of the instruction and completion of the predetermined motion.

2. The seat system according to claim 1, wherein the terminal is further configured to determine the performance level by comparing the response time and a reference response time as stored.

3. The seat system according to claim 1,
 wherein the sensor comprises a pressure sensor, and
 wherein the terminal is further configured to determine whether or not the occupant has made the predetermined motion based on a change in pressure acquired from the pressure sensor.

4. The seat system according to claim 1, wherein the terminal is further configured to output the instruction based on a magnitude of the differentiated value of the signal acquired from the sensor decreasing below a third threshold.

5. The seat system according to claim 1, wherein the terminal is further configured to output the instruction as chosen randomly from among a plurality of instructions.

6. The seat system according to claim 1, wherein the terminal is further configured to:
 execute a plurality of rounds of a process comprising outputting the instruction and determining the response time, and
 notify the occupant of an average of response times acquired in the plurality of rounds of the process and/or of a performance level evaluated based on the average of the response times.

7. The seat system according to claim 1, further comprising:
 a server configured to communicate with the terminal,
 wherein the terminal is configured to:
  store an attribute of the occupant, and
  transmit the response time and the attribute of the occupant to the server, and
 wherein the server is configured to accumulate the attribute and the response time for the occupant.

8. A computer program product comprising at least one non-transitory computer-readable storage medium having one or more program instructions stored therein to be executed on a terminal capable of acquiring information from a sensor provided at a seat body, the program instructions being configured to cause the terminal to execute operations comprising:
 outputting an instruction to prompt an occupant seated on the seat body to make a predetermined motion;
 acquiring the information from the sensor;
 determining, based on the information acquired from the sensor, whether or not the occupant has made the predetermined motion, the determining comprising:
  determining a differentiated value of a signal acquired from the sensor;
  determining that the predetermined motion has started based on a magnitude of the differentiated value having crossed a first threshold;
  determining that the predetermined motion has been completed based on the magnitude of the differentiated value having crossed the first threshold and then becoming less than a second threshold that is not more than the first threshold; and notifying the occupant of a response time or a performance level evaluated based on the response time or both, the response time comprising at least one time selected from the group consisting of a reaction time elapsed between the outputting of the instruction and the making of the predetermined motion, and a motion completion time elapsed between the outputting of the instruction and completion of the predetermined motion.

9. The computer program product according to claim 8, wherein the outputting comprises outputting the instruction based on the magnitude of the differentiated value of the signal acquired from the sensor decreasing below a third threshold value.

10. The computer program product according to claim 8, wherein the outputting comprises outputting the instruction as chosen randomly from among a plurality of instructions.

\* \* \* \* \*